United States Patent
Harayama et al.

(10) Patent No.: US 10,597,631 B2
(45) Date of Patent: Mar. 24, 2020

(54) GREEN ALGAE MUTANT EXHIBITING RESISTANCE TO INTENSE LIGHT, AND USE THEREOF

(71) Applicant: DENSO CORPORATION, Aichi (JP)

(72) Inventors: Shigeaki Harayama, Tokyo (JP); Jumpei Hayakawa, Tokyo (JP); Yoko Ide, Tokyo (JP); Yuki Tanaka, Tokyo (JP); Satoko Komatsu, Aichi (JP); Minoru Kurata, Aichi (JP)

(73) Assignee: DENSO CORPORATION, Kariya, Aichi (JP)

( * ) Notice: Subject to any disclaimer, the term of this patent is extended or adjusted under 35 U.S.C. 154(b) by 0 days.

(21) Appl. No.: 15/779,874

(22) PCT Filed: Nov. 30, 2016

(86) PCT No.: PCT/JP2016/085585
§ 371 (c)(1),
(2) Date: May 30, 2018

(87) PCT Pub. No.: WO2017/094785
PCT Pub. Date: Jun. 8, 2017

(65) Prior Publication Data
US 2018/0371401 A1    Dec. 27, 2018

(30) Foreign Application Priority Data

Dec. 1, 2015    (JP) ................. 2015-234736

(51) Int. Cl.
| | | |
|---|---|---|
| *C12N 1/12* | (2006.01) | |
| *C12P 7/64* | (2006.01) | |
| *C12N 15/82* | (2006.01) | |
| *C07K 14/405* | (2006.01) | |

(52) U.S. Cl.
CPC . *C12N 1/12* (2013.01); *C12P 7/64* (2013.01)

(58) Field of Classification Search
CPC ............. C12N 1/12; C12P 7/6463; C12P 7/64
See application file for complete search history.

(56) References Cited

U.S. PATENT DOCUMENTS 9,932,554 B2 * 4/2018 Im .................... C12M 21/02
2015/0337255 A1   11/2015 Kurata et al.

FOREIGN PATENT DOCUMENTS

JP      2014-117202 A    6/2014

OTHER PUBLICATIONS

Takahashi, S. et al., "Photoprotection in plants: a new light on photosystem Ii damage", Trends in Plant Science, 2011, vol. 16, No. 1 (pp. 53-60).
Tokutsu, R. et al., "Energy-dissipative supercomplex of photosystem II associated with LHCSR3 in Chlamydomonas reinhardtii", Proceedings of the National Academy of Sciences, 2013, vol. 110, No. 24 (pp. 10016-10021).
Singh, S.P. et al., "Effect of temperature and light on the growth of algae species: A review", Renewable and Sustainable Energy Reviews, 2015, vol. 50 (pp. 431-444).
Masojidek, J. et al., "Productivity correlated to photobiochemical performance of Chlorella mass cultures grown outdoors in thin-layer cascades", Journal of industrial microbiology & biotechnology, vol. 38 No. 2 (pp. 307-317).
Kasai, Y. et al., "Construction of a self-cloning system in the unicellular green alga Pseudochoricystis ellipsoidea", Biotechnology for Biofuels, 2015, vol. 8, No. 1 (pp. 1-12).
Matsuwaki, I. et al., "Assessment of the biological invasion risks associated with a massive outdoor cultivation of the green alga, Pseudochoricystis ellipsoidea", Algal Research, 2015, vol. 9 (pp. 1-7).
Schierenbeck, L. et al., "Fast forward genetics to identify mutations causing a high light tolerant phenotype in Chlamydomonas reinhardtii by whole-genome-sequencing", BMC Genomics, 2015, vol. 16, No. 1 (p. 57).
Biedermann, S. et al., "WD40 and CUL4-based E3 ligases: lubricating all aspects of life", Trends in Plant Science, 2011, vol. 16, No. 1 (pp. 38-46).
Chen, S. et al., "Photoreceptor Specificity in the Light-Induced and COP1-Mediated Rapid Degradation of the Repressor of Photomorphogenesis SPA2 in *Arabidopsis*", PLOS Genetics, 2015, vol. 11, No. 9, e1005516 (22 pages total).

* cited by examiner

*Primary Examiner* — Ganapathirama Raghu
(74) *Attorney, Agent, or Firm* — Lucas & Mercanti, LLP

(57) ABSTRACT

While green algae are expected to serve as raw materials of biomass fuels, they are damaged by high-intensity light when subjected to mass-culture outdoors in summer, and biomass productivity is deteriorated as a consequence. In order to overcome such a drawback, the present invention provides a high-intensity light resistant green algae mutant that can be subjected to outdoor culture in summer. Specifically, the present invention relates to such green algae mutant, wherein functions or expression levels of a protein having a response regulatory domain at the N-terminus and a WD40 domain at the C-terminus are lower than those in a wild-type strain, and wherein said green algae mutant grows faster than a wild-type strain when cultured at a light intensity of 1,000, 1,500, or 2,000 µmol photons $m^{-2}$ $s^{-1}$ measured as photosynthetically active radiation (PAR).

11 Claims, 7 Drawing Sheets

Specification includes a Sequence Listing.

SEQUENCE LISTING

<160> NUMBER OF SEQ ID NOS: 5

<210> SEQ ID NO 1
<211> LENGTH: 12289
<212> TYPE: DNA
<213> ORGANISM: Pseudochoricystis ellipsoidea

<400> SEQUENCE: 1

```
cgggtgtctc aacttggacg tctaaatttt tgttgtttgc tttatgacca gggaagatct      60
ttctggaggt actttcaaat ctgatcgcaa aaatgttaat tcatgatcct gtaagctgcg     120
gtgcgaaagg ggtgcgcgct tgaacagccc cacttcaggt taaaaatatg gcttctgtgg     180
aagctccttg cacgcccgct gacagcgggt gtcagccgag cacttctggc gtgaagacgt     240
caaagacagt agctcccaac gacgtgcata ttttgctcgt ggatgacgag cggctgtcgc     300
gcgttgtcgt tggcaatctg ctgcggaagt gctcttacaa aggtgtgcca cgttgcccag     360
gatatcttgg tgaatctttc agcccaatgt tggaaacgaa aattaaatta aaaatgttgt     420
tgtggtgtta atcttaccat attgaagtgt atcgtgcgtt gaggcccaca atccaaggag     480
taattctgtt ccacaattac agtgactgaa gctgggagcg gaatggaagc gctggaaatc     540
ttgagagggc agcctccagg gacattcagc ttggttttaa cggtgagatt tcttctggct     600
tctgttttga cgaccaagat ctgatgtttg cgtaaattat gatgcagacg tctaagccct     660
tttgctctgt cccaggacgt gatgatgccg gacgtggacg gcatagaact cctcaggcat     720 gtcagggtg acgaggcctg gagcaatctg ccagtcatca gtgagaaccc cttctttctg     780
ccctgcttcg gtgaatgaag agccgtggca gaggtcttta aatgaggaga gtcttggaga     840
gactgcagat gatttgcgtt gaggctgcat gttcactacc tggcaaggaa cgtggtccat     900
gtctttcctc tctatgcttg catagttgct tacagtgtgt acaaatgtgc tgcagtgatg     960
tcagccaacg aacggacaga gacagtcttc gagtgcatcc gaggaggagc agaggactat    1020
cttttaaaac cagtgacgaa gaaggaagtg cagcacatgt ggcagcatgt ttggcgtcgc    1080
caacaacaga atgcccttcg cgtgccgcac atgtgcccag aagacgtgag tcatctcatc    1140
cttctccaaa gtcagcttca cagggcaacg tcacattcca ttccattcct gctagcagtg    1200
tcttgcttgt gatatctggt atgcatgttg gtagtaccaa cttggtgccc taccctcgag    1260
tctgcttggt gcccagcagg ccatttgtcc ttcaatgcag catgtagcca agtcgctgcc    1320
atgtctgcag cccatttgca cccatcttgg gctgttccca gactgcctta atacaacccc    1380
acgctacact tctcatatac tcttagacaa tgtcccaatc ggacatggag ttgtcaccat    1440
ttcaagcacc acatgatcaa gttgaagtgg ggttgcgagt ggaggttgct actgctacta    1500
catgataaaa tataatggat attgtagaaa tatatgtaac atgaaagcgg gtggggatca    1560
tgacagtgtt gtgtacactt gtatgtaagc ctagtaataa gtaattatgt agtctgagta    1620
```

-continued

```
aattaaatat tgcaggcgga ggacttcctg cgagcgcaca gcacaacagc gtcagtgccg    1680
agcgcgccgc tgagtgtcgt gcaagcgtca gcggaggctc tggagactaa tttggaacag    1740
aagcagccgg cgcagtctgg ggcaagcagc ggcgagcagc cgatggagcg cgagagtgat    1800
ctccaaaggg atcagtcgga gggcagctct ttgccgccac ccgtgagtg  catcataggt    1860 tgcttgaaga gcaccttccg ctcacatttt gcaatgagat catttctgca taggaaggcc    1920
atgtcaggca gtggactggg ctggactgtt ttgagtatca gagaagcttc tcatgggaga    1980
gatgagctgg ggttgtcctg cctgcagtgg aacatgtgcc ctgcaattgc agtggaaaga    2040
ccgattccat ctatcttctt atctagttgt gctatcttaa gagcggcaaa actgtgttga    2100
tttagagcgt gctatctgag gtgggacttg ctgttggcca ggaccaaacc aggcgcagga    2160
cagagaagaa gaggacaggg aacggcggca atcagggtcg caagcaagcg catcagccgc    2220
atcggtgccg ggtcggcccg gggaggccgc ggcggtgggg ggcgcccccc ggggcggcgg    2280
cagccggggg atcccccggg tgtcagccgc cgcgcggcgg ggggaccccgc cggccgcacc   2340 gcccccgacg ctcgtgtcct actttggccg ccgcgggtcc acgatccgcc cggcagactc    2400
cttccgcatc ttctgcggcg tcttgtcgct gctcaaaacg ctgcatgcgc gcggcgtcac    2460
gctgcgccgc gtgcggccgt ccatgcttcg catcaccctcc agcggggtga gcccacttgc    2520
accgctctac attaacccac actgagatgc tgaggcttcc gaactctctc aatatattgt    2580
tgagcaatgc ctgatcaacc ttgtgacttg ctgttctctt gctccttttt ctgtgggtgg    2640
gttttcaggg attatgtcac atggtgaaca gtcatgccgt ggtcacatgc agagaactgt    2700
catgtgctat gtcaagcaca gccaaggcca tctgcagcac atagttccca gtcccagcaa    2760
cttccttcct ctgtaccagt gcccgagcac acatgtgtca tgcaggtggc ggtgtcgagc    2820
agcgcagtgc cgattccaga ggaggagtcc atgtatgcat caccggagga gctgctgtcg    2880
gggggcgcga acgtgtcgcc caagagcgac gtgtactcgc tgggcgtgct cttcttcgag    2940
ctgttcaacc cggtcagcga tgaggtggag cgcggccgcg ccctgcaggc gctccgccac    3000
cgaatcctgc cgccacatgt gctgcaggtt agcagtcccc tggaagtcag agcagttttt    3060
taatcgatca gatgatctct gaagagtttt cgaaggtcct tctggccggt tgaaccacac    3120
gcgctgcagg tcagcagttc tccaaaagcc agagcagttt tcatggatca gatgatttct    3180
ggagagtttc tgaaggtctt ctcgggcctg ttgaaagcgg ggatgggaca aaatagatag    3240
tttgagtgat tcagatatct caaatctctc cagtgtaagc gcatgctaac aaatcataat    3300
cgaggcagta acccgcacgt gcatggcctc acatgaaagg ctcaggtact tgatctattg    3360
cttagctggc gctacttggt gcttagtcag ctagttctag caaagtacat gaaagctgtg    3420 gttttgcaa ggttcccggc ttcggaagct tcctctcatg accgtgtcat gaagtttcat    3480
gtctcaagag atattcgtcg tgatggctga ctggtgttct gattgttgtt ctgcaaattg    3540
cagacgaggc ctcaggaggc agcgtttgtg ctgtcgctgc tgcatcccga ccccgactgc    3600
cgcccaagcg tggatgccat agtgcgctca gagctgctgc tggcactgca caagtccatt    3660
cgccagcgca agcattcctc aggtggggag ggcgctccac ccactcactt gcccagtgaa    3720
gtgctatgca tggtataaag tcgatagtcg attaaataaa agagaagact atcttgttat    3780
agtccacatt cacccatggc ctgctctgaa tcataactgg gatctcaact cttcttaatg    3840
ttgccgcctc cggttctctg tttcaagcac tgcgaatttg ctacagcaca ggtttggtga    3900
tgggcacttc gatcctcaca ttgttgtgaa acaccttgtt tttttttttc atggtgtgga    3960
taggatttaa agcgacagat aaataattgg ttgttggctc ttatatttag tggatttatg    4020
```

```
tgcttgtcca ccttgacccg attttatcgt gtctcacaat tctataagat cgagtgcctg    4080
ttgttaaagt gcgctatggc gaatgcgcca tgagctgctc taagcagatg catgggagag    4140
atgttaaggg cacctgttaa gtccttccga tttgcagaaa aggtcttgat gcattgtacc    4200
atcacagagt gaagtgaagt ttgtcggctt gcgcaggtgc gagccaagcg gagacccaga    4260
agcaggagga ggagaggagg gcgcaggcag caaaggctgc ccagcgggca gatgcagctg    4320
cccacgcagc tgcccaagcc gaccaggaca tcctggtcga tttcctgcgc ctcatgcgcc    4380
aagccaaagt gcgcagcact ccctaccgag aaacatattt tctttgtggt gtctagcagc    4440
catgtagaca ggagtgattt agtgacttaa aagctgatgt tttggggaca acttgcttgg    4500
gagcttgcaa gtattctatc agtgctgcaa ggttactatg ctgtcgcctg cgcaaccaa     4560 tgaacaagaa cattgctgtc tctcaggtgc aagatgagct tcattataga gagagaggtt    4620
taggttgttc tgttgtcctg tgtgtctaaa agagagcgca gttcctgatt ctggtgctgc    4680
atgttgaaaa caggaggcag agggggagga gtgtgtggac cggctgggcg cgctggacgc    4740
tgacatcagg atggtgactc agcggttagc gagggtgact aacaacaacg tcccctgct    4800 ccccgacggc ctccagcgcg ccatgctctg caacaagcgt cccgagatca gcggcagccg    4860
gaaacgcaag tcctgcgacc tcgaacattc tcttgccgaa aacggcggcc gaagatctgc    4920
cgcgctgatg aagcccgcct ccggcccact cgaacagcca ggtactgtgc cacttttttc    4980
ctgtgctgtg aggatcgtct tagttcggct aggatgcaat tccaatcggg aatctcagat    5040
tcttcttcct tcgctgaaaa agttgcaatc tgttgagcat gactatgatg acatggcgtc    5100
tccgctcagg ccagatcagg tagaagtaag gcttctgtgc gtattttct tgcatgcctg     5160 tggtttgctt gttgcggtgg cgtgcaagag tgtgatgggg cgttttttgtt ttgatggagg    5220 ggcacagtca gggagagtgt tcctagcgg tccaggaaag gcgctcagtt ggagacatat    5280
aatttcaagt gctgatcatg gctgtcggca gtgtgcaatc ctgccactgc gtttcaaagt    5340
agccgttgag acacatgaca agtgactagt cggtgcaaaa attgtccaca ccgcttctct    5400
gcacagactc gctctgtgca tccacttgtt gtgaatgtcg aacgtatcaa tggcggtgtg    5460
tgatgcggaa gtttgttgcc cgtgcaggtg ccaatattgg caaggcgctc gaggcgaact    5520
ggcagcgcgt ctccagcgcg ttcccggccc tcgagagcgc cttcttcgcg cggcgcgagg    5580
ccctggccgc gcagcaggcc gcgggggaa taacagaccc tagcaccgca aaccctgctg     5640
cctccagcac cgcgcgccgc cttgtcgaac tgggcatcgg aggagggaac gccgcggggt    5700
cgggcctcct tagcggccac caaccagacc acctagcagc attcacccgc gacctcagca    5760
agtttgtgcg ctacagcaag ctcaaggtgg ggtgccacct gttagcaacc ctaaacccta    5820
aagtcccaaa ccctcaaccc aagaaaccct aatcctcgag gtgggccgcg acctcagcaa    5880
gtttgtgcgc cacagcaagc tctaggtggg gcgccagctg tcagcaaccc taaacactac    5940
atctaaaccc taaggtccca aaacccaaac ccaaaaaacc ctaatcctca aggtggggcg    6000
cgcctgctgt ctgggcctga gctgttctca gggatgtgta cttaaacaaa acaggattca    6060
taatgcatcg tgctgtcttt tcagttctat gtccatgtgc aactcagtgt tactagatct    6120
tgtcgcgagt taagcatcgt atatccctga cccctttggg gttgttagaa ccactgtgag    6180
ggattggcgg catggggcag gtgcagctgc gtcagattta gaattcaaca aatttgtttg    6240
tcgctgtgaa ctcctacatt ctcggattag ctgttttgac cccggtgttg gtgttgtcaa    6300
caggtgaagg ccacgctgca gtatgggac atgctgcaca ccgcggacat gctgtgctcc    6360
```

```
atctcttttg atcgcgacga cgagtacttc gccactgccg gcgtgtctcg gcgcatcaag    6420
gtgagcaagt tggccctatg atattgcatg gccccatggt gtagctgcag acacgctgtg    6480
tgtatgccct aatgccatta ggctttgggt ttgccgacct gtaataatag taataataat    6540
aataatgatg atgatgatga tgataatggc aacttccatt acagccacct gaccgagttg    6600
gcatcagcag cccggcacga cctatctcat cacacagggg caatgttttt gtgaagcacc    6660
tcataacaag gctactatta ttggtcttga gcatcttttg acgagtatgc cgctcgaaga    6720
tatgagttgg gtgcacacgc atgaagatcg gactaagcaa ttgatcagag gactcgagct    6780
tgtcaagagt cttctatccc gcccacattg tgatcacatt gatgtgtcca catgtgacga    6840
ctttaatgtg tctacagttg attacattga tctgtcccct ctgtgatgac attgatctgc    6900
tggtgtggca ggtgtacgca acatcggatg tgctggaggc gaattcggcg gtgcactgcc    6960
cgcggctgga gatggcgtcg cgctccaagc tcagctgcgt gagctggaac tcctacatca    7020
agcacctgct gctggccgcc gactacgacg gctgcctcgc gctctgggat gccgaggcga    7080
acgcctgcac cgccactttc gaggagcatg ccaagcgcgt ctggtctgct gatttctccc    7140
aggtgctccc ctctttcttg aaggacgcca agtaaattc ggtaggtcta tgaggtccgt    7200
gggaattctg tgagctgcac atctgcttgt ggagttcaca gagtttcaga ggacctcata    7260
ggcctagcgt ctgctgactt ctcccaggtg ctccttctct tgttgcgcgg cgccaaagtg    7320
aatctggaag gtctatgagg ttctctgcaa attttgtgga cttcatgttt ccttgtggag    7380
ttcacgagag tttcagacga cctcataggc ctagcgtcgg cctgtcaggc atacggtatt    7440
gaactgggga tttaagttag tctgaggact ttgtgaaacc aggagtgact gggcatgcgt    7500
aagcttcctt gtggggtttt catggacata ctgcggttcc ttgaaagctg tctaagcaca    7560
tgtcaggcac atggcctccg tcataaacca gtaccttgca ttttggaggg ctcccacagg    7620
ataatgtatg tagacgcaca gactgccgat tgcggctgcc tgtaagcaca tatcacccgg    7680
tggcgagttc tttctgtgtc ggtcccggtg ctgtgaagat ttccttgctg acgtggactc    7740
acatggcaac gcagagcctc tgaaactcat tccaggtgc tctgtgtgcc atgtgaggga    7800
cttacagtag tatcttttcc tcttcctgaa tgcagcggtg attctgggtt ttacaaatag    7860
aaatccctgg ttggggtttg tagagcaaag tgtcttgagg agtgatttct gcgcgcagag    7920
cgacccgacg cgcttcgtgt ccggcagcga cgatggaaca gtgcggctgt ggagcattcg    7980
cgaggaggcg ccgaccgcgg tgatcgatgc caaggcgaat gtgtgcagcg tgcagttcag    8040
cccctcttgc gccaacctcc tggcgttcgg ctccgccaac taccgagtgt atctgtacga    8100
cctgcgccag atgcgggtgc ggcgcagaat gtgtcggagg aatttgaatt tgaaattgaa    8160
atcagaaggt gtctgggaat catcaacaca gttggcttct cctctgacag ttgccgcgtg    8220
agatgtaatt ttgtagatgt gtgggatgtg ctgcaatgct cttccacgcg tgcgactgcc    8280
tggcacactg ataagagtgt gcgaatccag atcccttcca tcctcaggtt gggaatctca    8340
cttgcttggc tgctggttgg tcaagagcct gcagagaatt ccggcagca acgaagcaag    8400 tgagcacctc aaccagaagt ttcaagggat ccaagcgcac agcattgcca tcgtcccgga    8460
ttcaatctag aaggttcaca aaccagctgt gcattcgaag gcttactgcg gcagtttcct    8520
ggcagatacc tgcttgtttt gactagtcta ggcggacttg tcaggtttca atcttggagc    8580
cgaaagccgt accgtgcctg acacattccg gaaccatcat atgtccctcc acacgctttg    8640
aattcatagg gctgtgaagt ggattatatt ttagggttta gggtttatat ttcatattta    8700
aggtttacat aataagtgtg tatatatagt cataaaccct aaatattcct aaaaccctaa    8760
```

-continued

```
gaatttaaca attaaaaaat ggatacatgg cgcgtgctgt gaagaactcg cagtgtggtg    8820
aatcaccgta gttgctctgt actgaggttg cttgcacatg caactggtac aggtaccatt    8880
ggcggtgatt gggggccatt cgaaggcggt gtcatatgtg cggtggctgg atggcacgca    8940
ccttgtgtcg gcgtccacgg ataaccagct caaattatgg gacctcgccg cggcgggccg    9000
ccatatgcgg cagcaggagt ggcggccgcg caccgttctc acaggtgatg agcccagaaa    9060
aatcagcgct ctacactcgc gcttgtgagc agagtttcac aaatgagcaa ttggctgggc    9120
gggttatctg gcggcagaca ctaaatcata tgagattggt ggcgcgctat agcatggata    9180
caagtctggc caagccacca ttggcttcga gaccgcgctc tgctcgccct tcttccacat    9240
ggagggagtc aaaaatatgt ccgagctcca tgttgtgagc ggcttcaagt gcaagaagca    9300
gcaatggtag ggcatgaccc tgtcatggcc ctgtcagcga tatcctcata ccaatcgctg    9360
gcgctccttg ctcttgaacc cgctgacaat gagaccctcg gataagtctt tgtaggcctt    9420
cgtgttaagt tgggatgggc agcgctgttt gaagttgat ggtcccatgg ccagacgctg     9480
tgtctgttct atagcgtgcc aaggtcctca tgccctgagc actcggcact ctcctgaagt    9540
tgacagagaa gctcaagatg caaaccggat tttttgcgat ctactagtgg ccattcctgc    9600
ctcatcgaag agtgcatcct tgtgaaagag gctggatttc aggccccaag tgtggcttct    9660
agacccttg cctgaaagta ctcttatgcc aaagcagtcc aggcagagtg cccacacgcc     9720
aatccagcga tgcaattctg aacaattggt ctgtttcgaa tgccaaatgg ctgtgcgtcg    9780
cacttagcaa ctcagggtac atggtgaaga tctctcaggt gaaggtctct taggtagagt    9840
taagagctgc cttttaggt tgggttaaga tctttgcttt tggctgacca atcccttgt      9900
tttattgcag ggcacacgaa cgagcgcaac tttgtgggct tgtcggtgac accggacggc    9960
tacatagcgt gcggcagcga agacaacagc gtgtacgcct acaccgcaac gctgccaaca    10020
cccctcgcgc gccactgctt cttcagctcg gagggctgcg ccgactcggt gcgccgcccc    10080
ctctttattt ctctcttcta ggggtttttt gggttttagg agtgctcttg acaagcccct    10140
cactgcgcca ctgcttctcc agcttcgagg gctgcgccga ctcggtgcgc cgccccttt     10200
ttatttctct cttctagggg ttttttgggt ttgaggaatg ctcttgacag gcccctcgcg    10260
cgccactgct tctccagctc ggagggttac gccgactcgg tgcgccgccc ctcttcattt    10320
ccctcttcta ggggtcccag gggttttcag ggttgttctt gaagctgtgg gccgccgtct    10380
catgcaaggc tcggtcctac tgtgctgaca cggtgcaatg ctcagtgcct tctagcactc    10440
cttcgcctgt accaaacgat tgtgtcggtg tgtttcggtc tctgcagagc tgcgcagagc    10500
tgcaagcact gtccaatgtg atggagtagt tttaggggag ctgcattgct gaattttagc    10560
aacaggcaga ggcagtgtat tgggcaaaag ttggacagta agaattgtgc gacttatact    10620
cctgatgttt agggtttagt gtagtgtagg ctacatttgg gcagcaggtc ttagggtcat    10680
gggcatacag taagaagtac tgcaggggct cgaatcagct tctaagtatg tctctgctgg    10740
ctggcgcagg aaggggagga gctcgcagtg gactcgcacc agtttgtgag cagcgtgtgc    10800
tggagccgca aggggcacac cctactcgct gccaactccc aaggcaccct caagctgctg    10860
gagctcgatt gagagttgca ctagtttcga gctcgaaagg atttccttcg cagctgatgg    10920
gcatgatgcg aggtgacttt ggtgctggcc gcctctccac aaggcaccct caagttgcta    10980
gagctggact gagttgcatc agtttcgagc tcgaaagggt tcttcgcag ctaatggata     11040
ttcagcgtgc cctttggtgc tggccgctta ttgacagggc accctcaggc tgctggacct    11100
```

-continued

```
gaaaatggaa ctcaattggc agttctaggg atgaggcctg cacatgaatg gatctgccaa    11160
ggagcgtacg ctgctctggt tgcagctcaa caaaaggtgc tggagctctg cgtgactctg    11220
aacaagactc gaagaaatga gtgttttgc tcatggaagc actgctccgt tgaccgtatg     11280
cagtaaagtg tggcatctgc tgctcatcag tgcagagttt atgaatcttt gaaggcgctg    11340
cttgttcttc gagtcggtgt catgggggc ggcagatttc aagtacatga cagccctgct    11400
gtcactttca taaggagcgc agcgggggc ctgaaacatc tagcactggg tgatcaaagg    11460
tgctcgtgaa atgttccgca cgtataacaa acggagtttc aaaagaggta gtgaaaggtg    11520
gacttgcggc gtgatatcag tgggctttgg caaaggaaaa tttggagtgt atcaatggga    11580
gtggagtaat gggggagatt gcacaaagtt gacgatacaa tctggcgctc caacaaggga    11640
ctcttgggga ccaccgtgtg caaattgctt tgtattggcg gcaactgccg cctgtcttct    11700
tcaaaggata tcatatcctt gagcgcactg atttgtgaca ttagcaggga ttgagtccag    11760
caggatacaa tccttgttgg agggtctgat cccaaacagc tgtctgaagt ggcagtcgat    11820
atgaagaccc tggccttgtt ctgcctagga acgatcctca tgtgctgagg ctcaacactg    11880
taggacgcaa tggggcgttt gggttcaagt gccaaactcg atctttaccg atgtgcctct    11940
cacatcgttg ggcctggtca caatgctatt cctggcgact tggctcgccg ccttgactga    12000
gaagagttgt gagagctggt gcggcgtttg gtgcacctgt tgaacggttg tgttccatgt    12060
tcgtcaaatt tggtattctt tgctttggag gagaaccggc gtgcgggtc tgaggttttc     12120 attgctttgg agttgaacat aagcagtgga aattggcaag acagggagac tcgttgctga    12180
ttctcgcaga gtatgaatg ttgtggctgc agtgtgcaca tgtgccacct ggatccacat     12240
ggatcctgaa tcaagattta ctgtaaagtg ctggctgagg aaaaagaag               12289

<210> SEQ ID NO 2
<211> LENGTH: 3162
<212> TYPE: RNA
<213> ORGANISM: Pseudochoricystis ellipsoidea
<220> FEATURE:
<221> NAME/KEY: CDS
<222> LOCATION: (1)..(3162)

<400> SEQUENCE: 2 aug gcu ucu gug gaa gcu ccu ugc acg ccc gcu gac agc ggg ugu cag     48
Met Ala Ser Val Glu Ala Pro Cys Thr Pro Ala Asp Ser Gly Cys Gln
1               5                   10                  15 ccg agc acu ucu ggc gug aag acg uca aag aca gua gcu ccc aac gac     96
Pro Ser Thr Ser Gly Val Lys Thr Ser Lys Thr Val Ala Pro Asn Asp
            20                  25                  30 gug cau auu uug cuc gug gau gac gag cgg cug ucg cgc guu guc guu    144
Val His Ile Leu Leu Val Asp Asp Glu Arg Leu Ser Arg Val Val Val
        35                  40                  45 ggc aau cug cug cgg aag ugu ucu uac aaa gug acu gaa gcu ggg agc    192
Gly Asn Leu Leu Arg Lys Cys Ser Tyr Lys Val Thr Glu Ala Gly Ser
    50                  55                  60 gga aug gaa gcg cug gaa auc uug aga ggg cag ccu cca ggg aca uuc    240
Gly Met Glu Ala Leu Glu Ile Leu Arg Gly Gln Pro Pro Gly Thr Phe
65                  70                  75                  80 agc uug guu uua acg gac gug aug aug ccg gac gug gac ggc aua gaa    288
Ser Leu Val Leu Thr Asp Val Met Met Pro Asp Val Asp Gly Ile Glu
                85                  90                  95 cuc cuc agg cau guc agg ggu gac gag gcc ugg agc aau cug cca guc    336
Leu Leu Arg His Val Arg Gly Asp Glu Ala Trp Ser Asn Leu Pro Val
            100                 105                 110
```

-continued

| | | |
|---|---|---|
| auc aug aug uca gcc aac gaa cgg aca gag aca guc uuc gag ugc auc<br>Ile Met Met Ser Ala Asn Glu Arg Thr Glu Thr Val Phe Glu Cys Ile<br>115                               120                        125 | 384 |
| cga gga gga gca gag gac uau cuu uua aaa cca gug acg aag aag gaa<br>Arg Gly Gly Ala Glu Asp Tyr Leu Leu Lys Pro Val Thr Lys Lys Glu<br>130                             135                      140 | 432 |
| gug cag cac aug ugg cag cau guu ugg cgu cgc caa caa cag aau gcc<br>Val Gln His Met Trp Gln His Val Trp Arg Arg Gln Gln Gln Asn Ala<br>145                         150                      155                160 | 480 |
| cuu cgc gug ccg cac aug ugc cca gaa gac gcg gag gac uuc cug cga<br>Leu Arg Val Pro His Met Cys Pro Glu Asp Ala Glu Asp Phe Leu Arg<br>165                      170                      175 | 528 |
| gcg cac agc aca aca gcg uca gug ccg agc gcg ccg cug agu guc gug<br>Ala His Ser Thr Thr Ala Ser Val Pro Ser Ala Pro Leu Ser Val Val<br>180                      185                      190 | 576 |
| caa gcg uca gcg gag gcu cug gag acu aau uug gaa cag aag cag ccg<br>Gln Ala Ser Ala Glu Ala Leu Glu Thr Asn Leu Glu Gln Lys Gln Pro<br>195                      200                      205 | 624 |
| gcg cag ucu ggg gca agc agc ggc gag cag ccg aug gag cgc gag agu<br>Ala Gln Ser Gly Ala Ser Ser Gly Glu Gln Pro Met Glu Arg Glu Ser<br>210                             215                      220 | 672 |
| gau cuc caa agg gau cag ucg gag ggc agc ucu uug ccg cca ccc gga<br>Asp Leu Gln Arg Asp Gln Ser Glu Gly Ser Ser Leu Pro Pro Pro Gly<br>225                         230                      235                240 | 720 |
| cca aac cag gcg cag gac aga gaa gaa gag gac agg gaa cgg cgg caa<br>Pro Asn Gln Ala Gln Asp Arg Glu Glu Glu Asp Arg Glu Arg Arg Gln<br>245                      250                      255 | 768 |
| uca ggg ucg caa gca agc gca uca gcc gca ucg gug ccg ggu cgg ccc<br>Ser Gly Ser Gln Ala Ser Ala Ser Ala Ala Ser Val Pro Gly Arg Pro<br>260                      265                      270 | 816 |
| ggg gag gcc gcg gcg gug ggg ggc gcc ccc cgg ggc ggc ggc agc cgg<br>Gly Glu Ala Ala Ala Val Gly Gly Ala Pro Arg Gly Gly Gly Ser Arg<br>275                      280                      285 | 864 |
| ggg auc ccc ccg gug uca gcc gcc gcg cgg cgg ggg gac ccg ccg gcc<br>Gly Ile Pro Pro Val Ser Ala Ala Ala Arg Arg Gly Asp Pro Pro Ala<br>290                           295                      300 | 912 |
| gca ccg ccc ccg acg cuc gug ucc uac uuu ggc cgc cgc ggg ucc acg<br>Ala Pro Pro Pro Thr Leu Val Ser Tyr Phe Gly Arg Arg Gly Ser Thr<br>305                         310                      315                320 | 960 |
| auc cgc ccg gca gac ucc uuc cgc auc uuc ugc ggc guc uug ucg cug<br>Ile Arg Pro Ala Asp Ser Phe Arg Ile Phe Cys Gly Val Leu Ser Leu<br>325                      330                      335 | 1008 |
| cuc aaa acg cug cau gcg cgc ggc guc acg cug cgc cgc gug cgg ccg<br>Leu Lys Thr Leu His Ala Arg Gly Val Thr Leu Arg Arg Val Arg Pro<br>340                      345                      350 | 1056 |
| ucc aug cuu cgc auc acc ucc agc ggg gug gcg gug ucg agc agc gca<br>Ser Met Leu Arg Ile Thr Ser Ser Gly Val Ala Val Ser Ser Ser Ala<br>355                      360                      365 | 1104 |
| gug ccg auu cca gag gag gag ucc aug uau gca uca ccg gag gag cug<br>Val Pro Ile Pro Glu Glu Glu Ser Met Tyr Ala Ser Pro Glu Glu Leu<br>370                         375                      380 | 1152 |
| cug ucg ggg ggc gcg aac gug ucg ccc aag agc gac gug uac ucg cug<br>Leu Ser Gly Gly Ala Asn Val Ser Pro Lys Ser Asp Val Tyr Ser Leu<br>385                         390                      395                400 | 1200 |
| ggc gug cuc uuc uuc gag cug uuc aac ccg guc agc gau gag gug gag<br>Gly Val Leu Phe Phe Glu Leu Phe Asn Pro Val Ser Asp Glu Val Glu<br>405                      410                      415 | 1248 |
| cgc ggc cgc gcc cug cag gcg cuc cgc cac cga auc cug ccg cca cau<br>Arg Gly Arg Ala Leu Gln Ala Leu Arg His Arg Ile Leu Pro Pro His<br>420                         425                      430 | 1296 |

```
gug cug cag acg agg ccu cag gag gca gcg uuu gug cug ucg cug cug      1344
Val Leu Gln Thr Arg Pro Gln Glu Ala Ala Phe Val Leu Ser Leu Leu
            435                 440                 445 cau ccc gac ccc gac ugc cgc cca agc gug gau gcc aua gug cgc uca      1392
His Pro Asp Pro Asp Cys Arg Pro Ser Val Asp Ala Ile Val Arg Ser
        450                 455                 460 gag cug cug cug gca cug cac aag ucc auu cgc cag cgc aag cau ucc      1440
Glu Leu Leu Leu Ala Leu His Lys Ser Ile Arg Gln Arg Lys His Ser
465                 470                 475                 480 uca ggu gcg agc caa gcg gag acc cag aag cag gag gag agg agg          1488
Ser Gly Ala Ser Gln Ala Glu Thr Gln Lys Gln Glu Glu Arg Arg
                485                 490                 495 gcg cag gca gca aag gcu gcc cag cgg gca gau gca gcu gcc cac gca      1536
Ala Gln Ala Ala Lys Ala Ala Gln Arg Ala Asp Ala Ala Ala His Ala
        500                 505                 510 gcu gcc caa gcc gac cag gac auc cug guc gau uuc cug cgc cuc aug      1584
Ala Ala Gln Ala Asp Gln Asp Ile Leu Val Asp Phe Leu Arg Leu Met
        515                 520                 525 cgc caa gcc aaa gag gca gag ggg gag gag ugu gug gac cgg cug ggc      1632
Arg Gln Ala Lys Glu Ala Glu Gly Glu Glu Cys Val Asp Arg Leu Gly
        530                 535                 540 gcg cug gac gcu gac auc agg aug gug acu cag cgg uua gcg agg gug      1680
Ala Leu Asp Ala Asp Ile Arg Met Val Thr Gln Arg Leu Ala Arg Val
545                 550                 555                 560 acu aac aac aac guc ccc cug cuc ccc gac ggc cuc cag cgc gcc aug      1728
Thr Asn Asn Asn Val Pro Leu Leu Pro Asp Gly Leu Gln Arg Ala Met
                565                 570                 575 cuc ugc aac aag cgu ccc gag auc agc ggc agc cgg aaa cgc aag ucc      1776
Leu Cys Asn Lys Arg Pro Glu Ile Ser Gly Ser Arg Lys Arg Lys Ser
                580                 585                 590 ugc gac cuc gaa cau ucu cuu gcc gaa aac ggc ggc cga aga ucu gcc      1824
Cys Asp Leu Glu His Ser Leu Ala Glu Asn Gly Gly Arg Arg Ser Ala
        595                 600                 605 gcg cug aug aag ccc gcc ucc ggc cca cuc gaa cag cca ggu gcc aau      1872
Ala Leu Met Lys Pro Ala Ser Gly Pro Leu Glu Gln Pro Gly Ala Asn
        610                 615                 620 auu ggc aag gcu cuc gag gcg aac ugg cag cgc guc ucc agc gcg uuc      1920
Ile Gly Lys Ala Leu Glu Ala Asn Trp Gln Arg Val Ser Ser Ala Phe
625                 630                 635                 640 ccg gcc cuc gag agc gcc uuc uuc gcg cgg cgc gag gcc cug gcc gcg      1968
Pro Ala Leu Glu Ser Ala Phe Phe Ala Arg Arg Glu Ala Leu Ala Ala
                645                 650                 655 cag cag gcc gcg ggg gga aua aca gac ccu agc acc gca aac ccu gcu      2016
Gln Gln Ala Ala Gly Gly Ile Thr Asp Pro Ser Thr Ala Asn Pro Ala
        660                 665                 670 gcc ucc agc acc gcg cgc cgc cuu guc gaa cug ggc auc gga gga ggg      2064
Ala Ser Ser Thr Ala Arg Arg Leu Val Glu Leu Gly Ile Gly Gly Gly
        675                 680                 685 aac gcc gcg ggg ucg ggc cuc cuu agc ggc cac caa cca gac cac cua      2112
Asn Ala Ala Gly Ser Gly Leu Leu Ser Gly His Gln Pro Asp His Leu
        690                 695                 700 gca gca uuc acc cgc gac cuc agc aag uuu gug cgc uac agc aag cuc      2160
Ala Ala Phe Thr Arg Asp Leu Ser Lys Phe Val Arg Tyr Ser Lys Leu
705                 710                 715                 720 aag gug aag gcc acg cug cag uau ggg gac aug cug cac acc gcg gac      2208
Lys Val Lys Ala Thr Leu Gln Tyr Gly Asp Met Leu His Thr Ala Asp
                725                 730                 735 aug cug ugc ucc auc ucu uuu gau cgc gac gac gag uac uuc gcc acu      2256
Met Leu Cys Ser Ile Ser Phe Asp Arg Asp Asp Glu Tyr Phe Ala Thr
```

-continued

|     |     |     |     |     |     |     |     |     |     |     |     |     |     |     |     |
|-----|-----|-----|-----|-----|-----|-----|-----|-----|-----|-----|-----|-----|-----|-----|-----|
|     |     | 740 |     |     |     | 745 |     |     |     | 750 |     |     |     |     |     |
| gcc | ggc | gug | ucu | cgg | cgc | auc | aag | gug | uac | gca | aca | ucg | gau | gug | cug | 2304 |
| Ala | Gly | Val | Ser | Arg | Arg | Ile | Lys | Val | Tyr | Ala | Thr | Ser | Asp | Val | Leu |
|     |     | 755 |     |     |     | 760 |     |     |     | 765 |     |     |     |     |     |
| gag | gcg | aau | ucg | gcg | gug | cac | ugc | ccg | cgg | cug | gag | aug | gcg | ucg | cgc | 2352 |
| Glu | Ala | Asn | Ser | Ala | Val | His | Cys | Pro | Arg | Leu | Glu | Met | Ala | Ser | Arg |
|     | 770 |     |     |     | 775 |     |     |     | 780 |     |     |     |     |     |     |
| ucc | aag | cuc | agc | ugc | gug | agc | ugg | aac | ucc | uac | auc | aag | cac | cug | cug | 2400 |
| Ser | Lys | Leu | Ser | Cys | Val | Ser | Trp | Asn | Ser | Tyr | Ile | Lys | His | Leu | Leu |
| 785 |     |     |     | 790 |     |     |     | 795 |     |     |     | 800 |     |     |     |
| cug | gcc | gcc | gac | uac | gac | ggc | ugc | cuc | gcg | cuc | ugg | gau | gcc | gag | gcg | 2448 |
| Leu | Ala | Ala | Asp | Tyr | Asp | Gly | Cys | Leu | Ala | Leu | Trp | Asp | Ala | Glu | Ala |
|     |     |     |     | 805 |     |     |     | 810 |     |     |     | 815 |     |     |     |
| aac | gcc | ugc | acc | gcc | acu | uuc | gag | gag | cau | gcc | aag | cgc | guc | ugg | ucu | 2496 |
| Asn | Ala | Cys | Thr | Ala | Thr | Phe | Glu | Glu | His | Ala | Lys | Arg | Val | Trp | Ser |
|     | 820 |     |     |     | 825 |     |     |     | 830 |     |     |     |     |     |     |
| gcu | gau | uuc | ucc | cag | agc | gac | ccg | acg | cgc | uuc | gug | ucc | ggc | agc | gac | 2544 |
| Ala | Asp | Phe | Ser | Gln | Ser | Asp | Pro | Thr | Arg | Phe | Val | Ser | Gly | Ser | Asp |
| 835 |     |     |     | 840 |     |     |     | 845 |     |     |     |     |     |     |     |
| gau | gga | aca | gug | cgg | cug | ugg | agc | auu | cgc | gag | gag | gcg | ccg | acc | gcg | 2592 |
| Asp | Gly | Thr | Val | Arg | Leu | Trp | Ser | Ile | Arg | Glu | Glu | Ala | Pro | Thr | Ala |
|     | 850 |     |     |     | 855 |     |     |     | 860 |     |     |     |     |     |     |
| gug | auc | gau | gcc | aag | gcg | aau | gug | ugc | agc | gug | cag | uuc | agc | ccc | ucu | 2640 |
| Val | Ile | Asp | Ala | Lys | Ala | Asn | Val | Cys | Ser | Val | Gln | Phe | Ser | Pro | Ser |
| 865 |     |     |     | 870 |     |     |     | 875 |     |     |     | 880 |     |     |     |
| ugc | gcc | aac | cuc | cug | gcg | uuc | ggc | ucc | gcc | aac | uac | cga | gug | uau | cug | 2688 |
| Cys | Ala | Asn | Leu | Leu | Ala | Phe | Gly | Ser | Ala | Asn | Tyr | Arg | Val | Tyr | Leu |
|     |     |     | 885 |     |     |     | 890 |     |     |     | 895 |     |     |     |     |
| uac | gac | cug | cgc | cag | aug | cgg | gua | cca | uug | gcg | gug | auu | ggg | ggc | cau | 2736 |
| Tyr | Asp | Leu | Arg | Gln | Met | Arg | Val | Pro | Leu | Ala | Val | Ile | Gly | Gly | His |
|     |     | 900 |     |     |     | 905 |     |     |     | 910 |     |     |     |     |     |
| ucg | aag | gcg | gug | uca | uau | gug | cgg | ugg | cug | gau | ggc | acg | cac | cuu | gug | 2784 |
| Ser | Lys | Ala | Val | Ser | Tyr | Val | Arg | Trp | Leu | Asp | Gly | Thr | His | Leu | Val |
|     |     | 915 |     |     |     | 920 |     |     |     | 925 |     |     |     |     |     |
| ucg | gcg | ucc | acg | gau | aac | cag | cuc | aaa | uua | ugg | gac | cuc | gcc | gcg | gcg | 2832 |
| Ser | Ala | Ser | Thr | Asp | Asn | Gln | Leu | Lys | Leu | Trp | Asp | Leu | Ala | Ala | Ala |
|     | 930 |     |     |     | 935 |     |     |     | 940 |     |     |     |     |     |     |
| ggc | cgc | cau | aug | cgg | cag | cag | gag | ugg | cgg | ccg | cgc | acc | guu | cuc | aca | 2880 |
| Gly | Arg | His | Met | Arg | Gln | Gln | Glu | Trp | Arg | Pro | Arg | Thr | Val | Leu | Thr |
| 945 |     |     |     | 950 |     |     |     | 955 |     |     |     | 960 |     |     |     |
| ggg | cac | acg | aac | gag | cgc | aac | uuu | gug | ggc | uug | ucg | gug | aca | ccg | gac | 2928 |
| Gly | His | Thr | Asn | Glu | Arg | Asn | Phe | Val | Gly | Leu | Ser | Val | Thr | Pro | Asp |
|     |     |     | 965 |     |     |     | 970 |     |     |     | 975 |     |     |     |     |
| ggc | uac | aua | gcg | ugc | ggc | agc | gaa | gac | aac | agc | gug | uac | gcc | uac | acc | 2976 |
| Gly | Tyr | Ile | Ala | Cys | Gly | Ser | Glu | Asp | Asn | Ser | Val | Tyr | Ala | Tyr | Thr |
|     |     | 980 |     |     |     | 985 |     |     |     | 990 |     |     |     |     |     |
| gca | acg | cug | cca | aca | ccc | cuc | gcg | cgc | cac | ugc | uuc | uuc | agc | ucg | gag | 3024 |
| Ala | Thr | Leu | Pro | Thr | Pro | Leu | Ala | Arg | His | Cys | Phe | Phe | Ser | Ser | Glu |
|     |     | 995 |     |     |     | 1000 |    |     |     | 1005 |    |     |     |     |     |
| ggc | ugc | gcc | gac | ucg | gaa | ggg | gag | gag | cuc | gca | gug | gac | ucg | cac |     | 3069 |
| Gly | Cys | Ala | Asp | Ser | Glu | Gly | Glu | Glu | Leu | Ala | Val | Asp | Ser | His |     |
|     | 1010 |    |     |     | 1015 |    |     |     | 1020 |    |     |     |     |     |     |
| cag | uuu | gug | agc | agc | gug | ugc | ugg | agc | cgc | aag | ggg | cac | acc | cua |     | 3114 |
| Gln | Phe | Val | Ser | Ser | Val | Cys | Trp | Ser | Arg | Lys | Gly | His | Thr | Leu |     |
|     | 1025 |    |     |     | 1030 |    |     |     | 1035 |    |     |     |     |     |     |
| cuc | gcu | gcc | aac | ucc | caa | ggc | acc | cuc | aag | cug | cug | gag | cuc | gau |     | 3159 |
| Leu | Ala | Ala | Asn | Ser | Gln | Gly | Thr | Leu | Lys | Leu | Leu | Glu | Leu | Asp |     |
|     | 1040 |    |     |     | 1045 |    |     |     | 1050 |    |     |     |     |     |     |
| uga |     |     |     |     |     |     |     |     |     |     |     |     |     |     |     | 3162 |

<210> SEQ ID NO 3
<211> LENGTH: 1053
<212> TYPE: PRT
<213> ORGANISM: Pseudochoricystis ellipsoidea

<400> SEQUENCE: 3

```
Met Ala Ser Val Glu Ala Pro Cys Thr Pro Ala Asp Ser Gly Cys Gln
1               5                   10                  15

Pro Ser Thr Ser Gly Val Lys Thr Ser Lys Thr Val Ala Pro Asn Asp
            20                  25                  30

Val His Ile Leu Leu Val Asp Asp Glu Arg Leu Ser Arg Val Val Val
        35                  40                  45

Gly Asn Leu Leu Arg Lys Cys Ser Tyr Lys Val Thr Glu Ala Gly Ser
    50                  55                  60

Gly Met Glu Ala Leu Glu Ile Leu Arg Gly Gln Pro Pro Gly Thr Phe
65                  70                  75                  80

Ser Leu Val Leu Thr Asp Val Met Met Pro Asp Val Asp Gly Ile Glu
                85                  90                  95

Leu Leu Arg His Val Arg Gly Asp Glu Ala Trp Ser Asn Leu Pro Val
            100                 105                 110

Ile Met Met Ser Ala Asn Glu Arg Thr Glu Thr Val Phe Glu Cys Ile
        115                 120                 125

Arg Gly Gly Ala Glu Asp Tyr Leu Leu Lys Pro Val Thr Lys Lys Glu
    130                 135                 140

Val Gln His Met Trp Gln His Val Trp Arg Arg Gln Gln Gln Asn Ala
145                 150                 155                 160

Leu Arg Val Pro His Met Cys Pro Glu Asp Ala Glu Asp Phe Leu Arg
                165                 170                 175

Ala His Ser Thr Thr Ala Ser Val Pro Ser Ala Pro Leu Ser Val Val
            180                 185                 190

Gln Ala Ser Ala Glu Ala Leu Glu Thr Asn Leu Glu Gln Lys Gln Pro
        195                 200                 205

Ala Gln Ser Gly Ala Ser Ser Gly Glu Gln Pro Met Glu Arg Glu Ser
    210                 215                 220

Asp Leu Gln Arg Asp Gln Ser Glu Gly Ser Ser Leu Pro Pro Pro Gly
225                 230                 235                 240

Pro Asn Gln Ala Gln Asp Arg Glu Glu Asp Arg Glu Arg Arg Gln
                245                 250                 255

Ser Gly Ser Gln Ala Ser Ala Ser Ala Ala Ser Val Pro Gly Arg Pro
            260                 265                 270

Gly Glu Ala Ala Ala Val Gly Gly Ala Pro Arg Gly Gly Gly Ser Arg
        275                 280                 285

Gly Ile Pro Pro Val Ser Ala Ala Arg Arg Gly Asp Pro Pro Ala
    290                 295                 300

Ala Pro Pro Pro Thr Leu Val Ser Tyr Phe Gly Arg Arg Gly Ser Thr
305                 310                 315                 320

Ile Arg Pro Ala Asp Ser Phe Arg Ile Phe Cys Gly Val Leu Ser Leu
                325                 330                 335

Leu Lys Thr Leu His Ala Arg Gly Val Thr Leu Arg Arg Val Arg Pro
            340                 345                 350

Ser Met Leu Arg Ile Thr Ser Ser Gly Val Ala Val Ser Ser Ser Ala
        355                 360                 365

Val Pro Ile Pro Glu Glu Glu Ser Met Tyr Ala Ser Pro Glu Glu Leu
```

```
                370             375             380
Leu Ser Gly Gly Ala Asn Val Ser Pro Lys Ser Asp Val Tyr Ser Leu
385             390             395             400

Gly Val Leu Phe Phe Glu Leu Phe Asn Pro Val Ser Asp Glu Val Glu
            405             410             415

Arg Gly Arg Ala Leu Gln Ala Leu Arg His Arg Ile Leu Pro Pro His
            420             425             430

Val Leu Gln Thr Arg Pro Gln Glu Ala Ala Phe Val Leu Ser Leu Leu
            435             440             445

His Pro Asp Pro Asp Cys Arg Pro Ser Val Asp Ala Ile Val Arg Ser
450             455             460

Glu Leu Leu Leu Ala Leu His Lys Ser Ile Arg Gln Arg Lys His Ser
465             470             475             480

Ser Gly Ala Ser Gln Ala Glu Thr Gln Lys Gln Glu Glu Glu Arg Arg
            485             490             495

Ala Gln Ala Ala Lys Ala Ala Gln Arg Ala Asp Ala Ala His Ala
            500             505             510

Ala Ala Gln Ala Asp Gln Asp Ile Leu Val Asp Phe Leu Arg Leu Met
            515             520             525

Arg Gln Ala Lys Glu Ala Glu Gly Glu Glu Cys Val Asp Arg Leu Gly
530             535             540

Ala Leu Asp Ala Asp Ile Arg Met Val Thr Gln Arg Leu Ala Arg Val
545             550             555             560

Thr Asn Asn Asn Val Pro Leu Leu Pro Asp Gly Leu Gln Arg Ala Met
            565             570             575

Leu Cys Asn Lys Arg Pro Glu Ile Ser Gly Ser Arg Lys Arg Lys Ser
            580             585             590

Cys Asp Leu Glu His Ser Leu Ala Glu Asn Gly Gly Arg Arg Ser Ala
            595             600             605

Ala Leu Met Lys Pro Ala Ser Gly Pro Leu Glu Gln Pro Gly Ala Asn
            610             615             620

Ile Gly Lys Ala Leu Glu Ala Asn Trp Gln Arg Val Ser Ser Ala Phe
625             630             635             640

Pro Ala Leu Glu Ser Ala Phe Phe Ala Arg Arg Glu Ala Leu Ala Ala
            645             650             655

Gln Gln Ala Ala Gly Gly Ile Thr Asp Pro Ser Thr Ala Asn Pro Ala
            660             665             670

Ala Ser Ser Thr Ala Arg Arg Leu Val Glu Leu Gly Ile Gly Gly Gly
            675             680             685

Asn Ala Ala Gly Ser Gly Leu Leu Ser Gly His Gln Pro Asp His Leu
            690             695             700

Ala Ala Phe Thr Arg Asp Leu Ser Lys Phe Val Arg Tyr Ser Lys Leu
705             710             715             720

Lys Val Lys Ala Thr Leu Gln Tyr Gly Asp Met Leu His Thr Ala Asp
            725             730             735

Met Leu Cys Ser Ile Ser Phe Asp Arg Asp Asp Glu Tyr Phe Ala Thr
            740             745             750

Ala Gly Val Ser Arg Arg Ile Lys Val Tyr Ala Thr Ser Asp Val Leu
            755             760             765

Glu Ala Asn Ser Ala Val His Cys Pro Arg Leu Glu Met Ala Ser Arg
            770             775             780

Ser Lys Leu Ser Cys Val Ser Trp Asn Ser Tyr Ile Lys His Leu Leu
785             790             795             800
```

```
Leu Ala Ala Asp Tyr Asp Gly Cys Leu Ala Leu Trp Asp Ala Glu Ala
                805                 810                 815

Asn Ala Cys Thr Ala Thr Phe Glu Glu His Ala Lys Arg Val Trp Ser
            820                 825                 830

Ala Asp Phe Ser Gln Ser Asp Pro Thr Arg Phe Val Ser Gly Ser Asp
        835                 840                 845

Asp Gly Thr Val Arg Leu Trp Ser Ile Arg Glu Glu Ala Pro Thr Ala
    850                 855                 860

Val Ile Asp Ala Lys Ala Asn Val Cys Ser Val Gln Phe Ser Pro Ser
865                 870                 875                 880

Cys Ala Asn Leu Leu Ala Phe Gly Ser Ala Asn Tyr Arg Val Tyr Leu
                885                 890                 895

Tyr Asp Leu Arg Gln Met Arg Val Pro Leu Ala Val Ile Gly Gly His
                900                 905                 910

Ser Lys Ala Val Ser Tyr Val Arg Trp Leu Asp Gly Thr His Leu Val
            915                 920                 925

Ser Ala Ser Thr Asp Asn Gln Leu Lys Leu Trp Asp Leu Ala Ala Ala
        930                 935                 940

Gly Arg His Met Arg Gln Gln Glu Trp Arg Pro Arg Thr Val Leu Thr
945                 950                 955                 960

Gly His Thr Asn Glu Arg Asn Phe Val Gly Leu Ser Val Thr Pro Asp
                965                 970                 975

Gly Tyr Ile Ala Cys Gly Ser Glu Asp Asn Ser Val Tyr Ala Tyr Thr
                980                 985                 990

Ala Thr Leu Pro Thr Pro Leu Ala Arg His Cys Phe Phe Ser Ser Glu
            995                 1000                1005

Gly Cys Ala Asp Ser Glu Gly Glu Glu Leu Ala Val Asp Ser His
    1010                1015                1020

Gln Phe Val Ser Ser Val Cys Trp Ser Arg Lys Gly His Thr Leu
    1025                1030                1035

Leu Ala Ala Asn Ser Gln Gly Thr Leu Lys Leu Leu Glu Leu Asp
    1040                1045                1050

<210> SEQ ID NO 4
<211> LENGTH: 112
<212> TYPE: PRT
<213> ORGANISM: Pseudochoricystis ellipsoidea

<400> SEQUENCE: 4

Ser Arg Val Val Val Gly Asn Leu Leu Arg Lys Cys Ser Tyr Lys Val
1               5                   10                  15

Thr Glu Ala Gly Ser Gly Met Glu Ala Leu Glu Ile Leu Arg Gly Gln
            20                  25                  30

Pro Pro Gly Thr Phe Ser Leu Val Leu Thr Asp Val Met Met Pro Asp
        35                  40                  45

Val Asp Gly Ile Glu Leu Leu Arg His Val Arg Gly Asp Glu Ala Trp
    50                  55                  60

Ser Asn Leu Pro Val Ile Met Met Ser Ala Asn Glu Arg Thr Glu Thr
65                  70                  75                  80

Val Phe Glu Cys Ile Arg Gly Gly Ala Glu Asp Tyr Leu Leu Lys Pro
                85                  90                  95

Val Thr Lys Lys Glu Val Gln His Met Trp Gln His Val Trp Arg Arg
            100                 105                 110
```

```
<210> SEQ ID NO 5
<211> LENGTH: 285
<212> TYPE: PRT
<213> ORGANISM: Pseudochoricystis ellipsoidea

<400> SEQUENCE: 5

Asp His Leu Ala Ala Phe Thr Arg Asp Leu Ser Lys Phe Val Arg Tyr
 1               5                  10                  15

Ser Lys Leu Lys Val Lys Ala Thr Leu Gln Tyr Gly Asp Met Leu His
            20                  25                  30

Thr Ala Asp Met Leu Cys Ser Ile Ser Phe Asp Arg Asp Asp Glu Tyr
        35                  40                  45

Phe Ala Thr Ala Gly Val Ser Arg Arg Ile Lys Val Tyr Ala Thr Ser
    50                  55                  60

Asp Val Leu Glu Ala Asn Ser Ala Val His Cys Pro Arg Leu Glu Met
65                  70                  75                  80

Ala Ser Arg Ser Lys Leu Ser Cys Val Ser Trp Asn Ser Tyr Ile Lys
                85                  90                  95

His Leu Leu Leu Ala Ala Asp Tyr Asp Gly Cys Leu Ala Leu Trp Asp
            100                 105                 110

Ala Glu Ala Asn Ala Cys Thr Ala Thr Phe Glu Glu His Ala Lys Arg
        115                 120                 125

Val Trp Ser Ala Asp Phe Ser Gln Ser Asp Pro Thr Arg Phe Val Ser
    130                 135                 140

Gly Ser Asp Asp Gly Thr Val Arg Leu Trp Ser Ile Arg Glu Glu Ala
145                 150                 155                 160

Pro Thr Ala Val Ile Asp Ala Lys Ala Asn Val Cys Ser Val Gln Phe
                165                 170                 175

Ser Pro Ser Cys Ala Asn Leu Leu Ala Phe Gly Ser Ala Asn Tyr Arg
            180                 185                 190

Val Tyr Leu Tyr Asp Leu Arg Gln Met Arg Val Pro Leu Ala Val Ile
        195                 200                 205

Gly Gly His Ser Lys Ala Val Ser Tyr Val Arg Trp Leu Asp Gly Thr
    210                 215                 220

His Leu Val Ser Ala Ser Thr Asp Asn Gln Leu Lys Leu Trp Asp Leu
225                 230                 235                 240

Ala Ala Ala Gly Arg His Met Arg Gln Gln Glu Trp Arg Pro Arg Thr
                245                 250                 255

Val Leu Thr Gly His Thr Asn Glu Arg Asn Phe Val Gly Leu Ser Val
            260                 265                 270

Thr Pro Asp Gly Tyr Ile Ala Cys Gly Ser Glu Asp Asn
        275                 280                 285
```

GREEN ALGAE MUTANT EXHIBITING RESISTANCE TO INTENSE LIGHT, AND USE THEREOF

CROSS-REFERENCE TO RELATED APPLICATIONS

This application is a 371 of PCT/JP2016/085585, filed Nov. 30, 2016, which claims benefit of Japanese Patent Application No. 2015-234736 filed on Dec. 1, 2015.

TECHNICAL FIELD

The present invention relates to a green algae mutant that is resistant to high-intensity light and use thereof.

BACKGROUND ART

Photosynthetic organisms that undergo oxygen-generating photosynthesis comprise 2 photochemical systems PSI and PSII. The photochemical reaction in PSII is initiated when chlorophyll a molecules in the PSII reaction center are excited and electrons are transferred to the initial electron acceptor ($Q_A$). In order to efficiently excite chlorophyll a molecules in the reaction center, a structure in which a chlorophyll a/b-protein complex referred to as an "antenna pigment" surrounds the reaction center and the antenna pigment efficiently transfers the captured light energy to the reaction center is formed on the thylakoid membrane. When the light is intensified, the number of photons that can be accepted by the antenna pigment per unit time is increased, and the photosynthetic rate is increased as a consequence. However, the number of electrons that can be accepted by $Q_A$ per unit time is limited. Thus, the photosynthetic rate is substantially maximized at the light intensity referred to as a "light saturation point." Even if the light intensity is further increased, the photosynthetic rate would not be increased. If the light intensity is further increased to a significant extent, the photosynthetic rate would rather be decreased. A decrease in the photosynthetic rate caused by the high-intensity light is referred to as "photoinhibition."

Photoinhibition is often caused by a lowered PSII activity caused by a damaged D1 protein, which constitutes PSII. The D1 protein is damaged by light energy absorbed by manganese in the manganese cluster that also constitutes PSII. Such D1 protein damage is also observed under low-intensity light. Under low-intensity light, however, the damaged D1 protein is removed rapidly and replaced with a newly synthesized D1 protein. As a result of such rapid D1 protein repair, a PSII activity would not be lowered under low-intensity light. Under high-intensity light, however, an excess amount of light energy is absorbed by the antenna pigment, and an active oxygen species such as single oxygen is generated by the excessive reduction power. This active oxygen species inhibits novel synthesis of the D1 protein, the amount of the active D1 protein is decreased, and photoinhibition is then induced as a consequence (Takahashi, S., & Badger, M. R., 2011, Photoprotection in plants: a new light on photosystem II damage, Trends in plant science, 16 (1), 53-60).

In order to avoid generation of an excess amount of reduction power, photosynthetic organisms have a mechanism of converting excess light energy into heat energy (NPQ: non-photochemical quenching). In the case of Chlorophyta, the Viridiplantae (hereafter, referred to as "green algae"), a protein referred to as "LHCSR" has the shared responsibility of NPQ. LHCSR binds chlorophyll a/b to xanthophyll and it is in contact with the antenna pigment. The light energy absorbed by chlorophyll that is bound to LHCSR is transferred to xanthophyll, followed by thermal dissipation. LHCSR is also capable of thermal dissipation of the light energy accepted by the antenna pigment in the vicinity thereof. The C-terminus of LHCSR is exposed to the lumen inside the thylakoid membrane. When electron transfer is caused on the thylakoid membrane by the photosynthetic reaction, $H^+$ migrates from the outside (the stroma) to the inside (the lumen) of the thylakoid membrane, $H^+$ passes through ATP synthetase localized on the thylakoid membrane of the chloroplast, and it returns to the stroma while synthesizing ATP. When irradiated with high-intensity light, the amount of $H^+$ introduced into the lumen upon photosynthetic electron transfer becomes larger than the amount of $H^+$ discharged through the ATP synthetase, and a pH level of the lumen shifts toward a more acidic state. When the C-terminal amino acid sequence of LHCSR is exposed to a low pH state, LHCSR activity is enhanced, and efficiency of LHCSR-induced thermal dissipation is enhanced. In addition, the LHCSR gene is induced under high-intensity light, and the LHCSR content is increased. As such content is increased, the NPQ capacity is also increased. Since the LHCSR level is low and a pH level of the lumen is not low under low-intensity light, a majority of the light energy captured by the antenna pigment is transferred to the reaction center. Under high-intensity light, however, both the activity and the amount of LHCSR are increased, and a majority of the light energy captured by the antenna pigment would undergo thermal dissipation (Tokutsu, R., & Minagawa, J., 2013, Energy-dissipative supercomplex of photosystem II associated with LHCSR3 in *Chlamydomonas reinhardtii*, Proceedings of the National Academy of Sciences, 110 (24), 10016-10021).

In recent years, microalgae have drawn attention as raw materials of biomass fuels. Unlike land-dwelling creatures, microalgae live and grow in water. In an underwater region near the surface of water that is struck by sunlight in summer, microalgae also experience photoinhibition. However, photoinhibition occurs at different light intensities depending on microalgae species (Singh, S. P., & Singh, P., 2015, Effect of temperature and light on the growth of algae species: A review, Renewable and Sustainable Energy Reviews, 50, 431-444).

Such photoinhibition damages microalgae when they are cultured outdoors. When *chlorella* was cultured in a very shallow culture pool outdoors, for example, growth inhibition was particularly significant when the *chlorella* cell density was low. When the *chlorella* cell density is low, many *chlorella* cells receive sunlight directly from the sun, and photoinhibition leads to growth inhibition as a consequence (Masojidek, J., Kopecky, J., Giannelli, L., & Torzillo, G., 2011, Productivity correlated to photobiochemical performance of *Chlorella* mass cultures grown outdoors in thin-layer cascades, Journal of industrial microbiology & biotechnology, 38 (2), 307-317).

The *Pseudochoricystis ellipsoidea* (*P. ellipsoidea*) Obi strain, which is an unicellular green algae belonging to the class Trebouxiophyceae (hereafter, it is referred to as the "Obi strain"), can grow at a pH level of 3.5 or lower and such strain can be cultured in an open culture system disclosed in JP Patent Publication (Kokai) No. 2014-117202 A. Thus, studies concerning the use thereof for biomass fuel production have been in progress (Kasai, Y., Oshima, K., Ikeda, F., Abe, J., Yoshimitsu, Y., & Harayama, S., 2015, Construction of a self-cloning system in the unicellular green alga *Pseudochoricystis ellipsoidea*, Biotechnology for biofuels, 8 (1), 1-12; and Matsuwaki, I., Harayama, S., & Kato, M., 2015; Assessment of the biological invasion risks associated with a massive outdoor cultivation of the green alga, *Pseudochoricystis ellipsoidea*. Algal Research, 9, 1-7). When the Obi strain was cultured in outdoor raceway culture equipment in summer, however, strong growth inhibition was observed at a low cell density as described with regard to the *chlorella* cells.

As a solution to the problem resulting from such photoinhibition, a mutant that is resistant to photoinhibition may be separated. There was one report concerning separation of photoinhibition-resistant microalgae in the past. After the *Chlamydomonas reinhardtii* cells were irradiated with UV to induce mutagenesis, mutants that would grow under high-intensity light (2,500 µmol photons $m^{-2}$ $s^{-1}$) were selected, and 2 strains were separated. Both mutants had mutations in the gene with the gene ID of Cre02.g085050. Thus, this gene was designated as the putative light response signaling protein 1 (LRS1). LRS1 comprised evolutionary conserved domain sequences; i.e., the RING domain in the N-terminal amino acid sequence and the WD 40 domain in the C-terminal amino acid sequence. An example of a protein comprising such 2 domains is the COP1 protein existing in *Arabidopsis thaliana*. When the COP1 amino acid was compared with the LRS1 amino acid sequence, the degree of sequence homology was found to be high in the N-terminal and C-terminal domains, although significant homology was not observed in the central region (Schierenbeck, L., Ries, D., Rogge, K., Grewe, S., Weisshaar, B., & Kruse, O., 2015, Fast forward genetics to identify mutations causing a high light tolerant phenotype in *Chlamydomonas reinhardtii* by whole-genome-sequencing, BMC genomics, 16 (1), 57). In *Arabidopsis thaliana*, COP1 forms a complex with a protein referred to as "SPA1," and it forms an ubiquitin transferase (E3 ubiquitin ligase) together with a protein such as CUL4, RBX1, or DDB1. SPA1 comprises a kinase domain at the N-terminus and the WD40 domain at the C-terminus. The COP1 WD40 domain is considered to recognize the target protein of the ubiquitin transferase in combination with the SPA1 WD40 domain (Biedermann, S., & Hellmann, H., 2011, WD40 and CUL4-based E3 ligases: lubricating all aspects of life, Trends in plant science, 16 (1), 38-46). SPA1 is a protein constituting an ubiquitin transferase, SPA1 itself is ubiquitinated by many optical signals, and it is degraded by a proteasome (Chen, S., Lory, N., Stauber, J., & Hoecker, U., 2015, Photoreceptor Specificity in the Light-Induced and COP1-Mediated Rapid Degradation of the Repressor of Photomorphogenesis SPA2 in *Arabidopsis*, PLoS Genet, 11 (9), e1005516). Specifically, activity of the COP1/SPA1 complex of *Arabidopsis thaliana* is associated with transmission of many optical signals through regulation of its own activity. It is thus deduced that LRS1 of *Chlamydomonas* is also a protein associated with transmission of high-intensity light stress signals.

SUMMARY OF INVENTION

Technical Problem

As described above, green algae are expected to serve as raw materials of biomass fuels. If green algae are subjected to mass-culture outdoors in summer, however, they are damaged by high-intensity light, and biomass productivity is deteriorated. In order to overcome such a drawback, it is an object of the present invention to separate green algae mutants exhibiting resistance to high-intensity light and subject such green algae to outdoor culture in summer.

Solution to Problem

The present inventors have conducted concentrated studies in order to attain the above object. As a result, they succeeded in separating a plurality of mutants derived from the Obi strain exhibiting resistance to high-intensity light. They determined the total genome sequences of these mutants and analyzed a mutant gene. As a result, they discovered that all the intense-light-resistant mutants had a mutation in a gene consisting of the nucleotide sequence as shown in SEQ ID NO: 1. Since the amino acid sequence encoded by such gene was apparently different from the amino acid sequence of LRS1 associated with high-intensity light resistance of *Chlamydomonas*, the gene consisting of the nucleotide sequence as shown in SEQ ID NO: 1 was designated as "LRS2," and a protein encoded by the LRS2 gene would be referred to as the "LRS2 protein" hereinbelow. The LRS2 protein comprised a response regulatory domain at the N-terminus and a WD40 domain at the C-terminus. The number of proteins comprising a response regulatory domain at the N-terminus and a WD40 domain at the C-terminus detected in the UniProt database was not more than 10 (described below); however, a protein having homology to the LRS2 protein over the full length was found in green algae, such as Trebouxiophyceae and Prasinophyceae. This indicates that proteins closely related to the LRS2 protein existing in green algae constitute a new protein family, which has functions similar to those of the LRS2 protein of the Obi strain. Thus, the present inventors discovered that a mutation may be introduced into a protein of the LRS2 family existing in green algae, so that intense-light-resistant strains may be obtained from such green algae. This has led to the completion of the present invention.

Specifically, the present invention includes the following.
(1) A green algae mutant, wherein functions or expression levels of a protein having a response regulatory domain at the N-terminus and a WD40 domain at the C-terminus (hereafter referred to as a "RR-WD protein") are lower than those of a wild-type strain, and wherein said green algae mutant grows faster than a wild-type strain when cultured at a light intensity of 1,000, 1,500, or 2,000 µmol photons $m^{-2}$ $s^{-1}$ measured as photosynthetically active radiation (PAR).
(2) The green algae mutant according to (1), which synthesizes an RR-WD protein having an amino acid sequence different from that of a RR-WD protein of the wild-type strain.
(3) The green algae mutant according to (1), wherein functions of the RR-WD protein are lowered by lowering the expression level of a gene encoding the RR-WD protein.
(4) The green algae mutant according to (1), wherein activity of the RR-WD protein is lowered by lowering translation efficiency for a gene encoding the RR-WD protein.
(5) The green algae mutant according to any one of (1) to (4), which belongs to the class Trebouxiophyceae.
(6) The green algae mutant according to (5), which belongs to the genus *Pseudococcomyxa*.
(7) A method for producing a lipid comprising a step of culturing the green algae mutant according to any one of (1) to (6).

This description includes part or all of the content as disclosed in the description and/or drawings of Japanese Patent Application No. 2015-234736, which is a priority document of the present application.

Advantageous Effects of Invention

According to the present invention, a green algae with improved high-intensity light resistance can be produced. By culturing the green algae mutant according to the present invention, in addition, productivity of a lipid to be subjected to biofuel production in summer can be improved.

DESCRIPTION OF EMBODIMENTS

Figure 1:
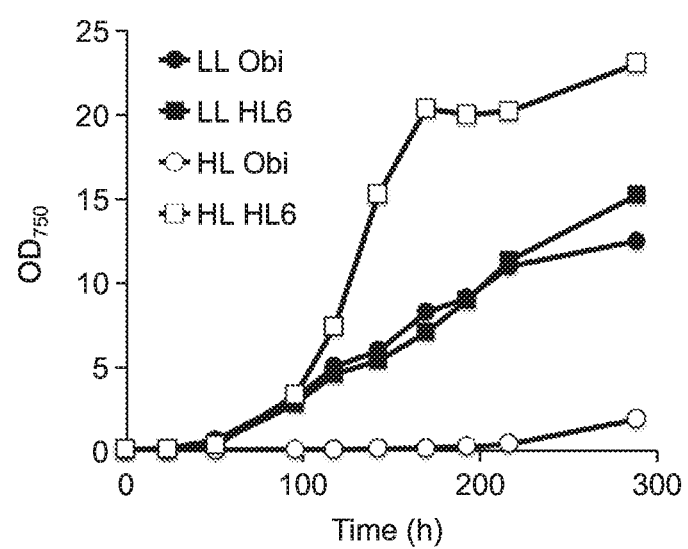
FIG. 1 shows a chart demonstrating the growth of the Obi strain and the HL6 strain under high-intensity light and under low-intensity light examined in Example 2. The vertical axis indicates $OD_{750}$ of the culture solution and the horizontal axis indicates a culture duration (h). LL indicates culture under low-intensity light (200 μmol photons $m^{-2}$ $s^{-1}$) and HL indicates culture under high-intensity light (2,000 μmol photons $m^{-2}$ $s^{-1}$).

The present invention relates to a green algae mutant that has acquired high-intensity light-resistance resulting from lowered functions or expression levels of a protein comprising a response regulatory domain at the N-terminus and a WD40 domain at the C-terminus (i.e., the RR-WD protein) than a wild-type strain, which grows faster than a wild-type strain under high-intensity light (e.g., when cultured at a light intensity of 1,000, 1,500, or 2,000 μmol photons $m^{-2}$ $s^{-1}$ measured as photosynthetically active radiation (PAR)). When producing biofuels and the like from green algae-derived lipids, the growth rate is lowered by photoinhibition under, in particular, intense sunlight in summer. The present inventors discovered that functions of the LRS2 protein consisting of the amino acid sequence as shown in SEQ ID NO: 3 derived from the Obi strain (DNA nucleotide sequence: SEQ ID NO: 1; mRNA nucleotide sequence: SEQ ID NO: 2) may be deleted, so that the growth of the green algae would be improved under high-intensity light. This has led to the completion of the present invention.

The LRS2 protein as shown in SEQ ID NO: 3 comprises a response regulatory domain at the N-terminus and a WD40 domain at the C-terminus. A protein comprising such domains may be detected on the InterPro site with the use of the function of "By Domain architecture" as found on the InterPro site. In such a case, the response regulatory domain may be detected with the use of the motif defined as IPR001789 or IPR011006. The WD40 domain may be detected with the use of the motif defined as IPR001680, IPR015943, IPR017986, or IPR019775.

A specific example of the RR-WD protein is a protein consisting of the amino acid sequence having the sequences which are at least 40%, preferably at least 45%, particularly preferably at least 50%, most preferably at least 60%, at least 70%, at least 80% or at least 90% identical to each of the amino acid sequences of the response regulatory domain as shown in SEQ ID NO: 4 and the WD40 domain as shown in SEQ ID NO: 5 of the LRS2 protein derived from the Obi strain, respectively, and having functions of the RR-WD protein.

An example of a gene encoding the RR-WD protein (hereafter, it is referred to as the "RR-WD protein-encoding gene") is a gene encoding a protein consisting of an amino acid sequence having at least 40%, preferably at least 45%, particularly preferably at least 50%, most preferably at least 60%, at least 70%, at least 80%, or at least 90% sequence identity to the amino acid sequence as shown in SEQ ID NO: 3 and having functions of the RR-WD protein.

Examples of functions of the RR-WD protein include functions as a constituent of an ubiquitin transferase.

In many green algae species, there may be a plurality of RR-WD protein-encoding genes, such as alleles and multiple genes. In the present invention, the RR-WD protein-encoding gene means at least one or a plurality of the RR-WD protein-encoding genes among them.

In the present invention, examples of organisms of green algae (Chlorophyta) include green algae of the genera *Chlorella* and *Pseudococcomyxa* belonging to the class Trebouxiophyceae. A specific example of a strain belonging to the class Trebouxiophyceae is the Obi strain (Accession Number FERM BP-10484; JP Patent No. 4,748,154 (referred to as the "*Pseudochoricystis ellipsoidea* Sekiguchi et Kurano gen. et sp. nov. MBIC11204" strain therein). The Obi strain was deposited at the International Patent Organism Depositary of the National Institute of Advanced Industrial Science and Technology (Tsukuba Central 6, 1-1, Higashi 1-chome, Tsukuba-shi, Ibaraki, 305-8566, Japan) as of Feb. 15, 2005 under Accession Number FERM P-20401 and then transferred to the international deposition under the provisions of the Budapest Treaty under Accession Number: FERM BP-10484. Further examples include green algae of the genera *Ostreococcus, Micromonas,* and *Bathycoccus* belonging to the class Prasinophyceae. Also, examples include green algae of the genus *Chlamydomonas* belonging to the class Chlorophyceae.

The green algae mutant according to the present invention is obtained by a method in which functions or expression levels of the RR-WD protein are lowered. According to the present invention, the green algae comprising the RR-WD protein-encoding gene may be subjected to the method in which functions or expression levels of the RR-WD protein encoded by the RR-WD protein-encoding gene are lowered. Thus, the green algae mutant according to the present invention can be obtained.

Examples of methods in which functions (or activity) or expression levels of the RR-WD protein are to be lowered include the following:

(1) a method of synthesizing an RR-WD protein comprising an amino acid sequence different from that of the wild-type RR-WD protein by substitution of the RR-WD protein-encoding gene sequence and substitution of a part of the amino acid sequence;

(2) a method of suppressing transcription of the RR-WD protein-encoding gene to lower the expression level of the gene; and (3) a method of suppressing translation of the RR-WD protein-encoding gene to lower translation efficiency of the gene.

(1) Method of Substituting the RR-WD Protein-Encoding Gene Sequence

In the present invention, a green algae mutant comprising a substitution in the RR-WD protein-encoding gene sequence inherently comprises a plurality of RR-WD protein-encoding genes, such as alleles and multiple genes, with at least one or a plurality of the RR-WD protein-encoding gene sequences among them being substituted.

According to a method of substitution of the RR-WD protein-encoding gene sequence, for example, a mutation involving substitution, deletion, insertion, and/or addition of a nucleotide is introduced into DNA of the RR-WD protein-encoding gene region on the genomic DNA of green algae or a promoter region located upstream thereof.

(2) Method of Suppressing Transcription of the RR-WD Protein-Encoding Gene to Lower the Expression Level of the Gene According to a method of suppressing transcription of the RR-WD protein-encoding gene, for example, a mutation is introduced into a transcription promoter region of the gene of the target green algae.

Alternatively, a mutation may be introduced into a sequence of a gene or DNA associated with positive expression control of the gene to lower functions thereof. In addition, a mutation may be introduced into a sequence of a gene or DNA associated with negative expression control of the gene, so that negative expression control would function constantly.

(3) Method of Suppressing Translation of the RR-WD Protein-Encoding Gene to Lower Translation Efficiency of the Gene An example of a method of suppressing translation of the RR-WD protein-encoding gene is so-called RNA interference (Cerutti H et al., 2011, Eukaryot Cell, 10, 1164).

Specifically, the green algae mutant according to the present invention in which functions or expression levels of the RR-WD protein are lowered can be produced in accordance with the procedure described in the Examples. More specifically, a mutagenic agent is allowed to react with a parent green algal strain, mutants that have acquired high-intensity light-resistance are screened for, and whether or not a mutation has occurred in the RR-WD protein-encoding gene sequence or expression in the obtained mutants is then confirmed.

As an example of the green algae mutant according to the present invention, the HL6 strain derived from the Obi strain described in the Examples was deposited at the National Institute of Technology and Evaluation, International Patent Organism Depositary (NITE-IPOD) (#120, 2-5-8 Kazusaka-matari, Kisarazu-shi, Chiba, 292-0818, Japan) as of Nov. 27, 2015 under Accession Number: FERM P-22299 and then transferred to the international deposition under the provisions of the Budapest Treaty under Accession Number: FERM BP-22299.

In addition, the present invention encompasses a method for producing a lipid comprising (mass-)culturing the green algae mutant according to the present invention described above to produce a lipid. As a method of mass-culture, for example, the culture method which has been already established and is disclosed in JP Patent Publication (Kokai) 2014-117202 A (the title of the invention: the method and the system for microalgae culture) can be employed. Specifically, green algae are cultured using a culture solution containing ammonia nitrogen (pH: 4 or less). According to such culture method, a pH level of the solution is 4 or less. Thus, other green algae and protists are less likely to grow. In particular, other microalgae and protists are less likely to grow since the culture solution contains ammonia nitrogen (e.g., urea). Thus, mass-culture can be easily realized outdoors. Even if $CO_2$ is introduced into a culture solution, also, bicarbonate ions are not generated, and a pH level of the culture solution is less likely to vary. In addition, a pH level of the medium after culture is not different from that before culture because of the use of urea as a nitrogen source. Thus, all or a part of green algae can be recovered from the culture solution used for green algae culture, and fresh green algae can be cultured with the use of the resulting culture solution. In such a case, a culture solution can be reused, and a cost for green algae culture can thus be reduced to a significant extent.

After culture, a lipid can be obtained from a culture product via hexane extraction or other means.

EXAMPLES

Hereafter, the present invention is described in greater detail with reference to the Examples, although the technical scope of the present invention is not limited to these Examples.

[Example 1] Separation of High-Intensity Light-Resistant Mutant

The Obi strain cultured in the MA5 medium (Imamura et al., 2012, J. Gen. Appl. Microbiol., 58, 1) was centrifuged to collect cells, and the collected cells were suspended in a citrate buffer (pH 6.0). To the resulting suspension, a mutagenic agent (i.e., NTG (1-methyl-3-nitro-1-nitrosoguanidine)) was added at 500 pig/ml, and the mixture was mildly agitated for 1 hour. Thereafter, the treated cells were cultured in the MA5 medium for 1 week with bubbling of 1% (v/v) $CO_2$ under fluorescent light at a PAR light intensity of 50 μmol photons $m^{-2}$ $s^{-1}$ (hereafter, light intensity is in terms of PAR). Thereafter, the cells were applied to the MA5 solid agar medium at $10^8$ cells/plate, and culture was conducted with the use of LED (455 nm, 660 nm) as a light source under high-intensity light (2,000 μmol photons $m^{-2}$ $s^{-1}$) for 2 weeks. Thereafter, the agar medium was transferred to the condition under fluorescent light (50 μmol photons $m^{-2}$ $s^{-1}$) and culture was conducted for an additional 1 week. Thus, 4 strains that were considered to exhibit a high viability under high-intensity light were isolated and designated as the HL6 strain, the HL7 strain, the HL9 strain, and the HL13 strain.

[Example 2] Evaluation of High-Intensity Light-Resistant Mutant

The HL6 strain, the HL7 strain, the HL9 strain, and the HL13 strain were cultured in the MA5 medium while adjusting $OD_{750}$ at 0.1 at a light intensity of 2,000 µmol photons $m^{-2}$ $s^{-1}$ with bubbling of 1% (v/v) $CO_2$. While the growth of the wild-type Obi strain was inhibited under high-intensity light, all the separated mutants were able to grow. The HL6 strain was cultured at a light intensity of 200 and 2,000 µmol photons $m^{-2}$ $s^{-1}$ and quantitatively evaluated. At a light intensity of 200 µmol photons $m^{-2}$ $s^{-1}$, no difference was observed in the growth between the Obi strain and the HL6 strain. At a light intensity of 2,000 µmol photons $m^{-2}$ $s^{-1}$, however, only the HL6 strain was able to grow (FIG. 1).

[Example 3] Evaluation of Lipid Productivity Under Different Light Conditions

Figure 2:
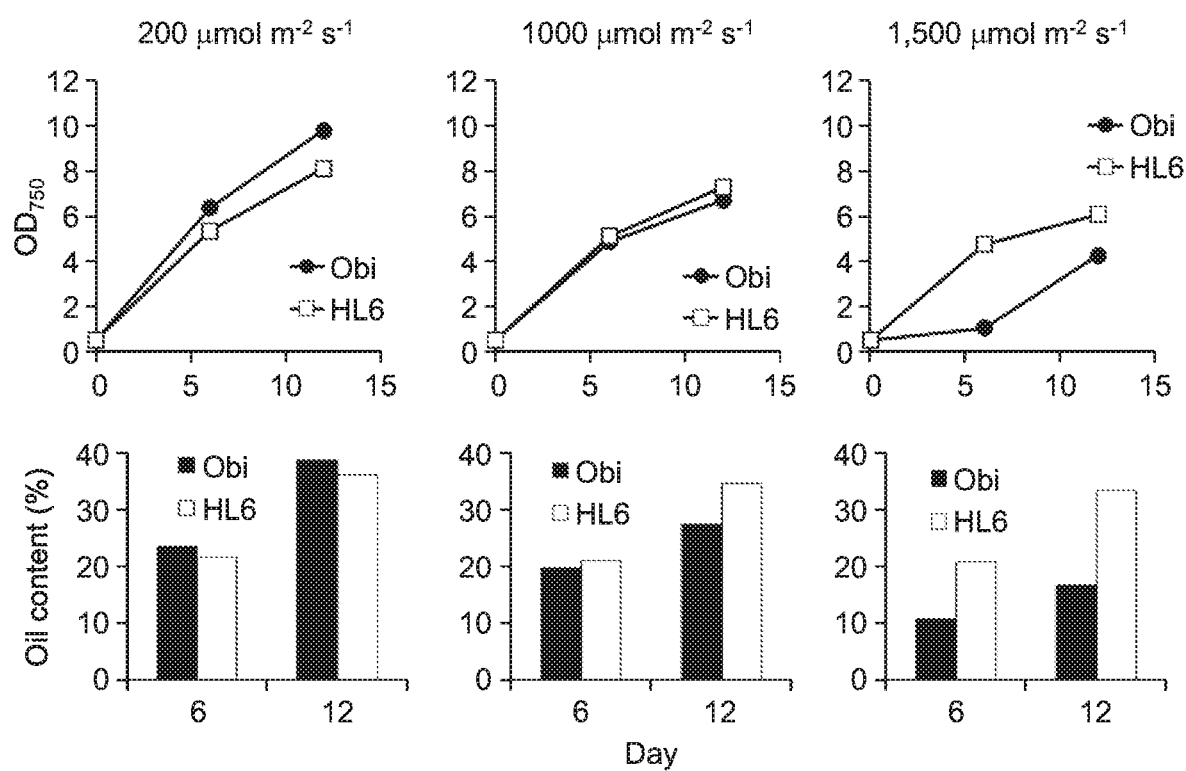
FIG. 2 shows charts demonstrating the growth and the lipid content of the Obi strain and the HL6 strain at different light intensities examined in Example 3. The light intensities were 200, 1,000, and 1,500 μmol photons $m^{-2}$ $s^{-1}$.

The separated high-intensity light-resistant mutant (the HL6 strain) and the parent strain thereof (the Obi strain) were cultured under 3 different light intensity conditions. The DENSO medium (2.38 mM $(NH_2)_2CO$, 863 µM $(NH_4)_2SO_4$, 405 µM $MgSO_4$, 265 µM $KH_2PO_4$, 264 µM $K_2HPO_4$, 61.2 µM $CaCl_2$, 1.20 µM $CuSO_4$, 1.13 µM $H_3BO_3$, 1.04 µM $ZnSO_4$, 0.622 µM $MnSO_4$, 0.294 µM $CoCl_2$, 12.4 nM $Na_2MoO_4$, 0.4% (v/v) Fe solution (3 g/l citric acid, 4.9 g/l1 ammonium ferric citrate, 0.5 g/l1 EDTA-2Na)) was diluted 2 fold and the resulting ½ DENSO medium was used. When culture was initiated, the cell density was $OD_{750}$ of 0.5 and the light intensity was 200, 1,000, or 1,500 µmol photons $m^{-2}$ $s^{-1}$. Cell sampling was carried out 6 days and 12 days after the initiation of culture. Concerning the Obi strain, the growth thereof and the amount of lipid accumulated therein decreased as the light intensity increased. While the growth of the HL6 strain and the amount of lipid accumulated therein decreased, the extent thereof was significantly suppressed, in comparison with that of the Obi strain. While the lipid productivity of the Obi strain was higher than that of the HL6 strain at 200 µmol photons $m^{-2}$ $s^{-1}$, the lipid productivity of the HL6 strain was superior to that of the Obi strain at any time under the light conditions of over 1,000 µmol photons $m^{-2}$ $s^{-1}$ (FIG. 2).

Figure 3:
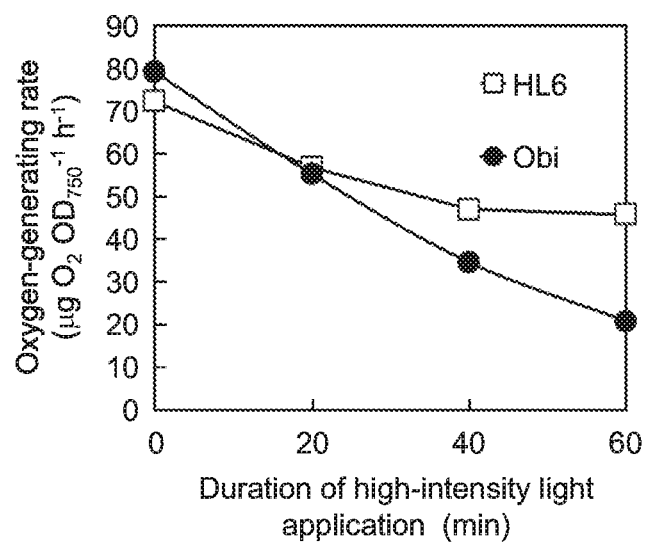
FIG. 3 shows a chart demonstrating the correlation between the duration of high-intensity light application and photosynthetic activity of the Obi strain and the HL6 strain examined in Example 4. The cells were irradiated with LED with light intensity of 2,000 μmol photons $m^{-2}$ $s^{-1}$.

[Example 4] Evaluation of Photoinhibition of Photochemical System II when Irradiated with High-Intensity Light The Obi strain and the HL6 strain were cultured under fluorescent light (50 µmol photons $m^{-2}$ $s^{-1}$) in the MA5 medium for 1 week, the cultured strains were diluted to $OD_{750}$ of 1.0 in the MA5 medium, and culture was then conducted with application of LED (2,000 µmol photons $m^{-2}$ $s^{-1}$). After the initiation of light application, the photosynthetic activity (the oxygen-generating rate) was assayed at the oxygen electrode every given period of time. As the light application time was prolonged, photosynthetic activity was lowered in the case of the Obi strain, and the photosynthetic activity was reduced to approximately 25% of the original level 1 hour after the initiation of light application. In contrast, the HL6 strain maintained 65% of the photosynthetic activity under the same conditions (FIG. 3).

[Example 5] NPQ Assay

An NPQ level can be evaluated by conducting chlorophyll fluorescence assay using an apparatus, Dual-PAM-100 (Waltz, Germany). Under fluorescent light (50 µmol photons $m^{-2}$ $s^{-1}$), the cells of the Obi strain and the HL6 strain cultured for 1 week were suspended in the MA5 medium containing 5 mM $NaHCO_3$ to adjust the chlorophyll concentration at 10 µg chl/ml. Before the assay was initiated, the strains were subjected to acclimatization in the dark for 5 minutes, the resulting strains were pulse-irradiated with a very low assay beam, and a change in the fluorescence level responded to the pulse was then assayed.

FIG. 4(A) shows a change in chlorophyll fluorescence levels in the Obi strain. When only an assay pulse beam is intermittently and continuously applied, a very low fluorescence was generated in response thereto ("FIG. 4a"). In this case, chlorophyll constituting an antenna pigment (i.e., antenna chlorophyll) absorbs the pulse light, the resulting excited energy is transferred to the reaction center, and part of the excited antenna chlorophyll generates fluorescence instead of transferring the excited energy to the reaction center. Subsequently, excitation light (1,300 µmol photons $m^{-2}$ $s^{-1}$) was applied as a continuous light. Under excitation light application, the amount of fluorescence generated in response to the assay pulse beam increased ("FIG. 4b") for the following reasons. That is, many PSII initial acceptors ($Q_A$) were reduced as a result of excitation light application, the excited antenna chlorophyll could not smoothly transfer the excited energy to the reaction center, and a greater quantity of fluorescence was generated as a consequence.

Figure 4:
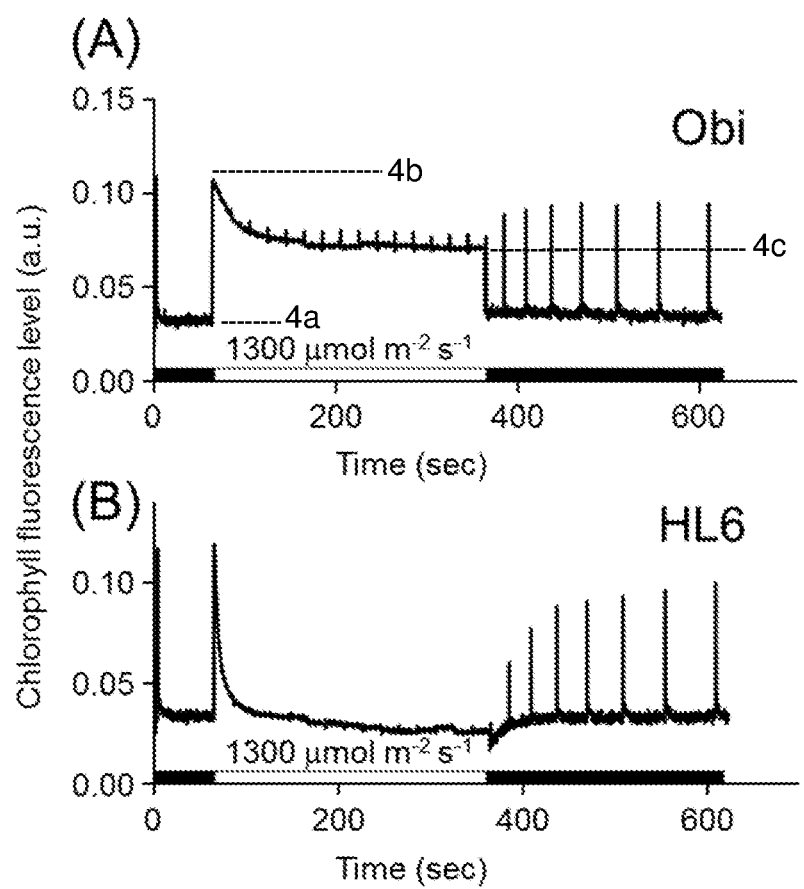
FIG. 4 shows a chart demonstrating a change in chlorophyll fluorescence levels measured as PAM in Example 5. (A) shows the Obi strain and (B) shows the HL6 strain. An excitation light of 1,300 μmol photons $m^{-2}$ $s^{-1}$ was applied over a period indicated in a white box on the horizontal axis.

With the elapse of the time after the initiation of excitation light application, the fluorescence level was lowered (fluorescence quenching; it is referred to as "FIG. 4c"). As an electron flows towards $Q_A$ or thermal dissipation of the antenna chlorophyll excitation energy takes place and quenching thus occurs, fluorescence level is lowered. The former quenching is referred to as "photochemical quenching," and the latter quenching is referred to as "non-photochemical quenching (NPQ)." A fluorescence spike observed in FIG. 4 is the fluorescence level after the application of a saturation pulse beam. As a result of application of a saturation pulse beam, $Q_A$ is completely reduced temporarily, and photochemical quenching becomes primarily zero as a consequence. A difference between the fluorescence level at the time of application of a saturation pulse beam and that before and after application of a saturation pulse beam indicates an extent of photochemical quenching. The value determined by subtracting the fluorescence level shown as FIG. 4c from the fluorescence level shown as FIG. 4b indicates quenching caused during excitation light application. This indicates that the proportion of photochemical quenching is small relative to the entire quenching.

FIG. 4(B) shows a change in chlorophyll fluorescence levels in the HL6 strain. In the case of the HL6 strain, the fluorescence level rapidly decreased; i.e., NPQ rapidly increased, within 30 seconds after excitation light application. Specifically, the HL6 strain was found to have a mechanism that realizes efficient thermal dissipation of the excessive excited energy. The HL6 strain is considered to have acquired high-intensity light resistance because of such efficient thermal dissipation.

[Example 6] Inspection of Xanthophyll Cycle Reaction

A component of NPQ is a xanthophyll cycle. A xanthophyll cycle is a reaction in which 3 types of xanthophylls, which are accessory antenna pigments, undergo dismutation. Of such 3 types of xanthophylls, Violaxanthin, which exhibits the lowest efficiency of thermal dissipation, has 2 epoxy rings. However, Violaxanthin is converted into Antheraxanthin, which exhibits low efficiency of thermal dissipation next to the lowest, by de-epoxidase, and it is further converted into Zeaxanthin, which exhibits the highest efficiency of thermal dissipation (i.e., de-epoxydation). The de-epoxidase is present in the lumen inside the thylakoid membrane, and an optimal pH level thereof is 5.0. Under high-intensity light, a pH of the lumen shifts toward an acidic state for the reason described above, and Zeaxanthin exhibiting high efficiency of thermal dissipation is accumulated. Under low-intensity light, however, such reaction is suppressed, and Violaxanthin exhibiting low efficiency of thermal dissipation is accumulated by an epoxidase that is present in the stroma outside of the thylakoid membrane. Whether or not the mechanism of such xanthophyll cycle differs between the Obi strain and the HL6 strain was inspected.

Figure 5:
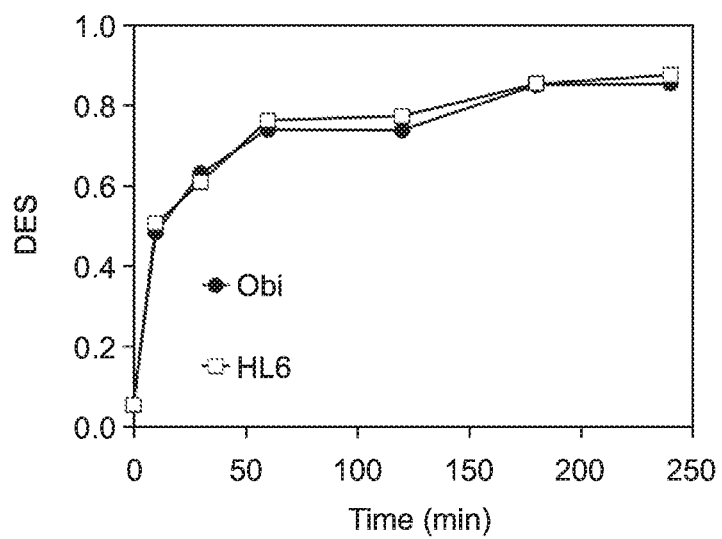
FIG. 5 shows a chart demonstrating a change in the De-epoxidation state (DES) index upon application of high-intensity light measured in Example 6. Similar changes were observed in the Obi strain and the HL6 strain.

The $OD_{750}$ value of the Obi strain and that of the HL6 strain cultured under fluorescent light (50 µmol photons $m^{-2}$ $s^{-1}$) were adjusted to 1.0 using the MA5 medium, and the light of 1,300 µmol photons $m^{-2}$ $s^{-1}$ was applied. Thereafter, sampling was carried out with the elapse of time, and the contents of the 3 xanthophylls in the xanthophyll cycle were analyzed via HPLC. On the basis of the results, the de-epoxidation state (DES) (i.e., $(Z+0.5 A)/(Z+A+V)$) indicating the amount of the de-epoxydated xanthophyll with high efficiency of thermal dissipation was determined. In the above-mentioned formula, Z represents Zeaxanthin content, A represents Antheraxanthin content, and V represents Violaxanthin content. No difference was observed in changes in such values with the elapse of time between the Obi strain and the HL6 strain (FIG. 5).

[Example 7] NPQ in the Obi Strain Acclimatized to High-Intensity Light

Figure 6:
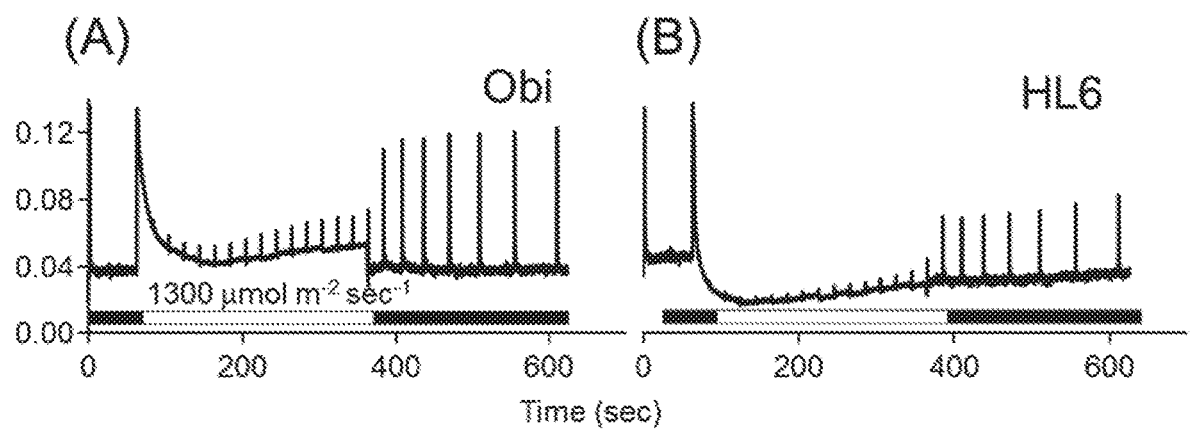
FIG. 6 shows charts demonstrating a change in chlorophyll fluorescence levels of the Obi strain (A) and the HL6 strain (B) cultured under high-intensity light in Example 7.

The Obi strain was cultured at a light intensity of 1,000 µmol photons $m^{-2}$ $s^{-1}$ for 2 days, and an NPQ level was measured using the cells. Unlike the NPQ level (FIG. 4) of the cells obtained from the Obi strain cultured under low-intensity light, the NPQ level of the cells obtained from the Obi strain acclimatized to high-intensity light was close to that of the HL6 strain that had also been cultured at a light intensity of 1,000 µmol photons $m^{-2}$ $s^{-1}$ for 2 days (FIG. 6). It was thus concluded that the Obi strain has a mechanism of NPQ induced when grown under high-intensity light and such mechanism is always active in the HL6 strain. On the basis of the studies on *Chlamydomonas*, this mechanism is considered to be LHCSR.

On the basis of the above, changes in chlorophyll fluorescence levels shown in FIGS. 4 and 6 can be understood as described below. In the case of the Obi strain grown under low-intensity light, electron flow from chlorophyll to $Q_A$ in the reaction center is restricted after excitation light application, and fluorescence is accordingly increased rapidly. As the photosynthetic electron transfer system functions, a pH of the lumen shifts toward an acidic state, and de-epoxidase is then activated. As a result, Zeaxanthin concentration is increased, and NPQ is accordingly increased with the elapse of time after the initiation of excitation light application. However, LHCSR is not induced within a short period of time, and an NPQ size is accordingly less than that of the HL6 strain. In the case of the HL6 strain and the Obi strain acclimatized to high-intensity light, in contrast, LHCSR is induced. As a pH of the lumen shifts toward an acidic state, LHCSR existing in large quantities is collectively activated, thermal dissipation is carried out immediately, and fluorescence levels are decreased rapidly as a consequence.

In the case of outdoor culture, the sunlight intensity rapidly changes, for example, in the presence of clouds. However, it takes several hours to induce SHCSR. Accordingly, the Obi strain may suffer from a fatal damage upon rapid exposure to high-intensity light. The HL6 strain is suitable for culture under such conditions.

[Example 8] Genomic Analysis of High-Intensity Light-Resistant Mutant

Figure 7:
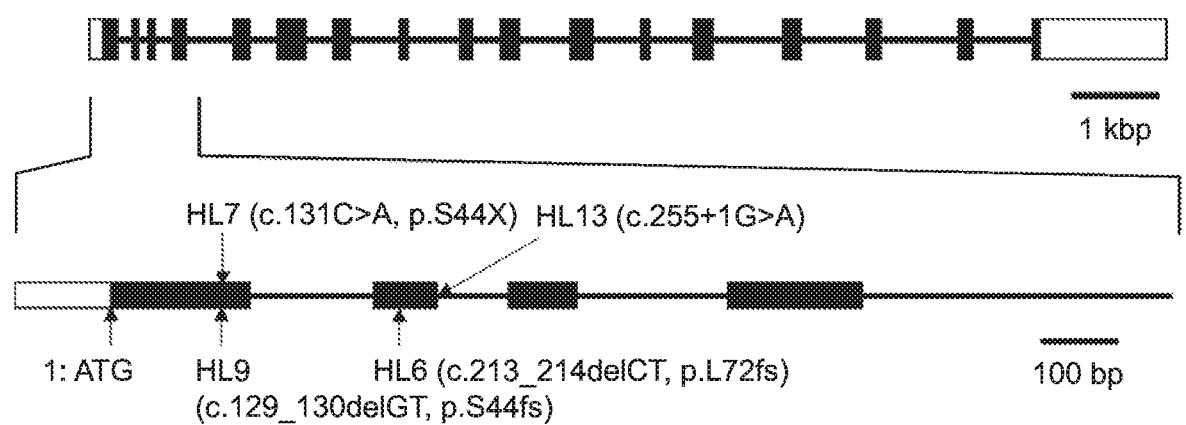
FIG. 7 schematically shows the structure of the LRS2 gene and sites of mutations in high-intensity light-resistant strains derived from the Obi strain. An un-translated region of the gene is indicated in a white rectangle and a translated region is indicated in a black rectangle. An exon is indicated with a line. Since mutations are concentrated at the 5' terminus of the gene, an enlarged view of such region is also shown.

The genomic nucleotide sequences of the 4 types of mutants derived from the Obi strain exhibiting high-intensity light resistance (i.e., the HL6 strain, the HL7 strain, the HL9 strain, and the HL13 strain) were determined using the Illumina HiSeq 2000 or Applied Biosystems 3730xl DNA analyzer, and mutation analysis was carried out. The LRS2 gene of the HL6 strain was lack of 2 nucleotides (C and T) at positions 213 and 214 in the coding region (CDS). As a result, a frameshift mutation occurred at a site downstream of the amino acid at position 72 (leucine (L)) (c.213_214delCT, p.L72fs). In the HL7 strain, nucleotide substitution (C-A) occurred at position 131 in CDS, and the amino acid at position 44 (serine (S)) was converted to a stop codon as a consequence (c.131C>A, p.S44X). The HL9 strain was lack of 2 nucleotides (G and T) at positions 129 and 130 in CDS. As a result, a frameshift mutation occurred at a site downstream of the amino acid at position 44 (serine (S)) (c.129_130delGT, p.S44fs). In the case of the HL13 strain, nucleotide substitution (G→A) occurred at a nucleotide next to nucleotide at position 255 located at the terminus of the second exon (i.e., the first nucleotide of the second intron), and normal splicing could not occur as a consequence (c.255+1G>A) (FIG. 7).

It was thus concluded that a mutation to acquire high-intensity light resistance would be induced by a mutation of the LRS2 gene. In addition, the LRS2 protein with partially conserved functions cannot be produced as a result of a non-sense mutation, a frameshift mutation, or the like. It was thus deduced that the LRS2 protein was not essential in terms of viability.

The amino acid sequence of the LRS2 protein was analyzed using ScanInterPro. As a result, the LRS2 protein was found to comprise a response regulatory domain at the N-terminus and a WD40 domain at the C-terminus. In order to detect a protein comprising such domains, analysis was carried out on the InterPro site with the use of the function of "By Domain architecture" as found on the InterPro site. In such a case, the response regulatory domain was detected with the use of the motif defined as IPR001789 or IPR011006, and the WD40 domain was detected with the use of the motif defined as IPR001680, IPR015943, IPR017986, or IPR019775. As a result, 6 proteins were detected as proteins comprising the response regulatory domain at the N-terminus and the WD40 domain at the C-terminus (the RR-WD proteins), and these proteins were found to be distributed among organisms of green algae (Chlorophyta). It was thus concluded that the RR-WD proteins constitute a very small protein family distributed in green algae and such proteins have equivalent functions. In addition, the genome of *Chlamydomonas* was further analyzed, and a protein deduced to be produced from the gene identified with Gene ID of Cre13.g602700 was found to be an RR-WD protein exhibiting a high degree of homology to the amino acid sequence of the LRS2 protein. In addition, a sequence encoding this RR-WD protein was detected in the Coccomyxa C-169 strain, which is closely related to *Pseudococcomyxa*. However, such sequence is considered to be registered as 2 separate peptides as a consequence of erroneous nucleotide sequence editing. In fact, it is considered that the RR-WD protein is also produced in the C-169 strain.

As with the case of SPA1 of *Arabidopsis thaliana*, the RR-WD proteins may be capable of forming a complex with COP1 and serving as a constituent of the ubiquitin transferase. Through ubiquitination of the target protein of the ubiquitin transferase, the RR-WD protein may be associated with transmission of high-intensity light signals.

While physiological functions of the RR-WD protein remain unknown, the present invention enabled production of a high-intensity light-resistant strain by lowering functions or expression levels of such protein via mutation or other means in a green algae strain comprising a protein of the same family. The present invention also realized improved productivity of a lipid to be subjected to biofuel production or the like via culture of the high-intensity light-resistant strain in an environment that receives intense light.

Accession Numbers
FERM BP-10484
FERM BP-22299

All publications, patents, and patent applications cited herein are incorporated herein by reference in their entirety.

The invention claimed is:

1. A green algae mutant, wherein functions or expression levels of a protein having a response regulatory domain at the N-terminus and a WD40 domain at the C-terminus are lower than those of a wild-type strain thereof, and wherein said green algae mutant grows faster than said wild-type strain by said lowered functions or expression levels of said protein, when cultured at a light intensity of 1,000, 1,500, or 2,000 µmol photons $m^{-2}s^{-1}$ measured as photosynthetically active radiation (PAR), and
    wherein said protein consists of an amino acid sequence having at least 90% sequence identity to the amino acid sequence of SEQ ID NO: 3 and has a function as a constituent of an ubiquitin transferase.

2. The green algae mutant according to claim 1, which synthesizes said protein having an amino acid sequence different from that of said protein of the wild-type strain.

3. The green algae mutant according to claim 1, wherein functions of said protein are lowered by lowering the expression level of a gene encoding said protein.

4. The green algae mutant according to claim 1, wherein activity of said protein is lowered by lowering translation efficiency for a gene encoding said protein.

5. The green algae mutant according to claim 1, which belongs to the class Trebouxiophyceae.

6. The green algae mutant according to claim 5, which belongs to the genus *Pseudococcomyxa*.

7. A method for producing a lipid comprising a step of culturing the green algae mutant according to claim 1.

8. The green algae mutant according to claim 2, which belongs to the class Trebouxiophyceae.

9. The green algae mutant according to claim 3, which belongs to the class Trebouxiophyceae.

10. The green algae mutant according to claim 4, which belongs to the class Trebouxiophyceae.

11. The green algae mutant according to claim 1, wherein said protein consists of the amino acid sequence as shown in SEQ ID NO: 3 and has a function as a constituent of an ubiquitin transferase.

* * * * *